United States Patent
Brockman et al.

(10) Patent No.: US 9,839,443 B2
(45) Date of Patent: Dec. 12, 2017

(54) SYSTEMS AND METHODS FOR OFF-AXIS TISSUE MANIPULATION

(71) Applicant: Stryker Corporation, Kalamazoo, MI (US)

(72) Inventors: Christopher Scott Brockman, Kalamazoo, MI (US); Gabriel James Harshman, Portage, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 1068 days.

(21) Appl. No.: 13/923,104

(22) Filed: Jun. 20, 2013

(65) Prior Publication Data

US 2013/0345765 A1 Dec. 26, 2013

Related U.S. Application Data

(60) Provisional application No. 61/662,223, filed on Jun. 20, 2012.

(51) Int. Cl.
*A61B 17/34* (2006.01)
*A61B 17/68* (2006.01)
(Continued)

(52) U.S. Cl.
CPC ...... *A61B 17/3472* (2013.01); *A61B 17/1642* (2013.01); *A61B 17/1757* (2013.01);
(Continued)

(58) Field of Classification Search
CPC ............ A61B 17/1631; A61B 17/1642; A61B 17/164; A61B 17/1644; A61B 1/005;
(Continued)

(56) References Cited

U.S. PATENT DOCUMENTS 6,383,190 B1 5/2002 Preissman
6,717,092 B2 * 4/2004 Obata ................. A61B 1/0011
219/127
(Continued)

FOREIGN PATENT DOCUMENTS

CA          2292521            10/2007
CH    WO 2011080104 A1 *   7/2011   ......... A61B 17/8877
JP        2007151595 A        6/2007

OTHER PUBLICATIONS

Paul Breedveld et al, A New, Easily Miniaturized Steerable Endoscope, IEEE Engineering in Medicine and Biology Magazine, Nov./Dec. 2005, 40-47.
(Continued)

*Primary Examiner* — Anu Ramana
(74) *Attorney, Agent, or Firm* — Howard & Howard Attorneys PLLC

(57) ABSTRACT

A surgical system and method for manipulating tissue. A steerable assembly comprises a steerable instrument and a deformable conduit. The steerable instrument comprises a control element and a deflectable portion operatively connected to the control element. The steerable assembly is directed through an access cannula such that at least a portion of the steerable assembly protrudes from the distal end of the access cannula. The steerable instrument is actuated to move a deflectable portion of the steerable instrument and a distal portion of the deformable conduit away from the longitudinal axis of the access cannula so that the deformable conduit assumes a deformed position. The steerable instrument is retracted from the deformable conduit.

12 Claims, 17 Drawing Sheets

(51) Int. Cl.
  *A61B 17/16* (2006.01)
  *A61B 17/17* (2006.01)
  *A61B 17/88* (2006.01)
  *A61B 17/00* (2006.01)

(52) U.S. Cl.
  CPC .......... *A61B 17/3478* (2013.01); *A61B 17/68* (2013.01); *A61B 17/8811* (2013.01); *A61B 17/8819* (2013.01); *A61B 17/8855* (2013.01); *A61B 2017/003* (2013.01); *A61B 2017/0034* (2013.01); *A61B 2017/00261* (2013.01); *A61B 2017/00314* (2013.01); *A61B 2017/00318* (2013.01); *A61B 2017/00323* (2013.01); *A61B 2017/00336* (2013.01)

(58) Field of Classification Search
  CPC ... A61B 1/0051; A61B 1/0052; A61B 1/0056; A61B 1/008; A61B 1/012; A61B 2017/003; A61B 2017/00305; A61B 2017/00309; A61B 2017/00314; A61B 2017/00318; A61B 2017/564; A61B 17/8816; A61B 17/8819; A61B 17/885; A61B 17/8805; A61B 17/7097
  See application file for complete search history.

(56) References Cited

U.S. PATENT DOCUMENTS

| | | | |
|---|---|---|---|
| 6,790,210 B1* | 9/2004 | Cragg | A61B 17/1617 606/180 |
| 6,875,219 B2 | 4/2005 | Arramon et al. | |
| 7,090,683 B2* | 8/2006 | Brock | A61B 34/20 606/1 |
| 7,682,364 B2 | 3/2010 | Reiley et al. | |
| 7,731,720 B2 | 6/2010 | Sand et al. | |
| 7,862,554 B2* | 1/2011 | Hegeman | A61B 1/0052 600/139 |
| 7,883,475 B2* | 2/2011 | Dupont | A61B 17/0469 600/585 |
| 7,918,874 B2 | 4/2011 | Siegal | |
| 7,959,634 B2 | 6/2011 | Sennett | |
| 8,114,097 B2* | 2/2012 | Brock | A61B 34/20 600/114 |
| 8,663,226 B2* | 3/2014 | Germain | A61B 17/1642 606/79 |
| 8,894,658 B2 | 11/2014 | Linderman et al. | |
| 9,113,974 B2* | 8/2015 | Germain | A61B 17/1642 |
| 9,168,078 B2 | 10/2015 | Linderman et al. | |
| 9,421,057 B2* | 8/2016 | Germain | A61B 17/1642 |
| 9,439,634 B2 | 9/2016 | Ries et al. | |
| 2003/0130664 A1 | 7/2003 | Boucher et al. | |
| 2003/0216685 A1 | 11/2003 | Porter | |
| 2004/0034369 A1* | 2/2004 | Sauer | A61B 1/00071 606/139 |
| 2004/0044270 A1* | 3/2004 | Barry | A61B 1/0056 600/142 |
| 2004/0127963 A1* | 7/2004 | Uchida | A61B 17/1671 607/96 |
| 2007/0093840 A1* | 4/2007 | Pacelli | A61B 17/1631 606/80 |
| 2008/0114364 A1 | 5/2008 | Goldin et al. | |
| 2009/0272388 A1* | 11/2009 | Uemura | A61B 17/0401 128/898 |
| 2010/0249759 A1* | 9/2010 | Hinman | A61B 1/008 606/1 |
| 2010/0298832 A1 | 11/2010 | Lau et al. | |
| 2011/0028991 A1* | 2/2011 | Ikeda | A61B 1/0052 606/130 |
| 2011/0295262 A1 | 12/2011 | Germain et al. | |
| 2012/0016367 A1 | 1/2012 | Chabansky et al. | |
| 2012/0130381 A1 | 5/2012 | Germain | |
| 2012/0143202 A1 | 6/2012 | Linderman | |
| 2012/0239047 A1 | 9/2012 | Linderman et al. | |
| 2012/0277755 A1 | 11/2012 | Liu et al. | |
| 2015/0297246 A1 | 10/2015 | Patel et al. | |

OTHER PUBLICATIONS

Bennie Mols, Movable tool tip for keyhole surgery, Delft Outlook, Mar. 2005, 13-17.
VersiTomic Flexible Reaming Systems, 2010,1-6, LJPVT-B Rev. 1, Mahwah, NJ.
Surgical Technique Guide and Product Catalog: Osseoflex Steerable Needle, Confidence Spinal Cement System, 2010, 1-18, DePuy Spine, Inc. Raynham, MA.
A new approach to kyphoplasty, CareFusion, 2011, 1-12, CareFusion Waukegan, IL.
Radiofrequency-Targeted Vertebral Augmentation, 2011, 1-2, DFINE Inc., San Jose, CA.
Experience the Power of Innovation, 2011, 1-4, NeuroTherm, Wilmington, MA.
KYPHON Balloon Kyphoplasty, Medtronic, 2011, 1-16, Medtronic, Memphis, TN.
International Search Report for Application No. PCT/US2013/046853 dated Aug. 29, 2013, 12 pages.
English language abstract and translation for JP2007151595 extracted from espacenet.com database Jan. 6, 2017, 25 pages.

* cited by examiner

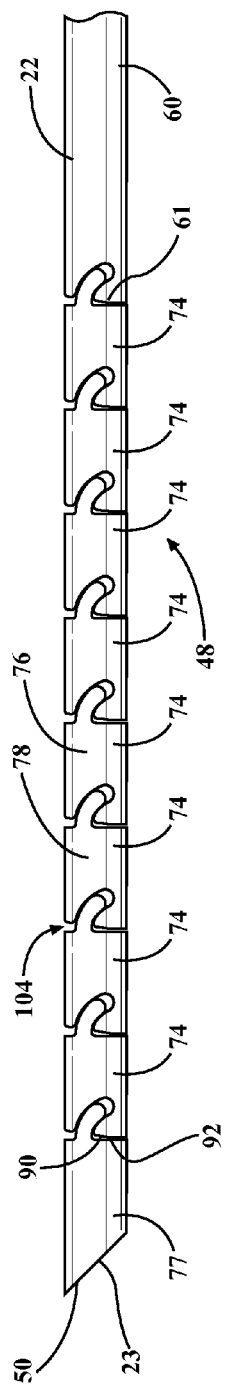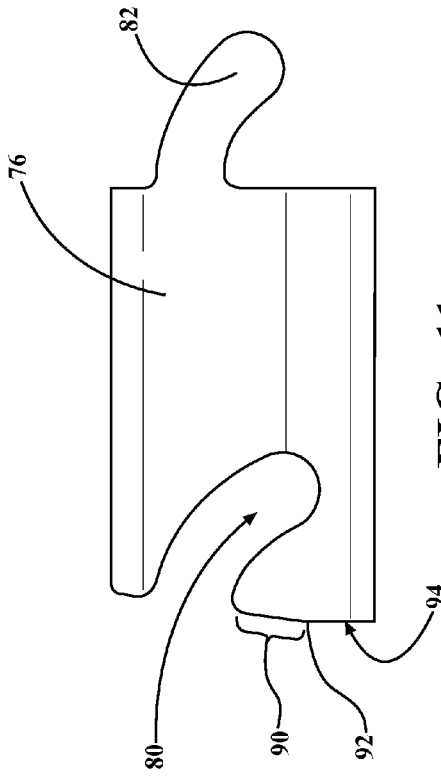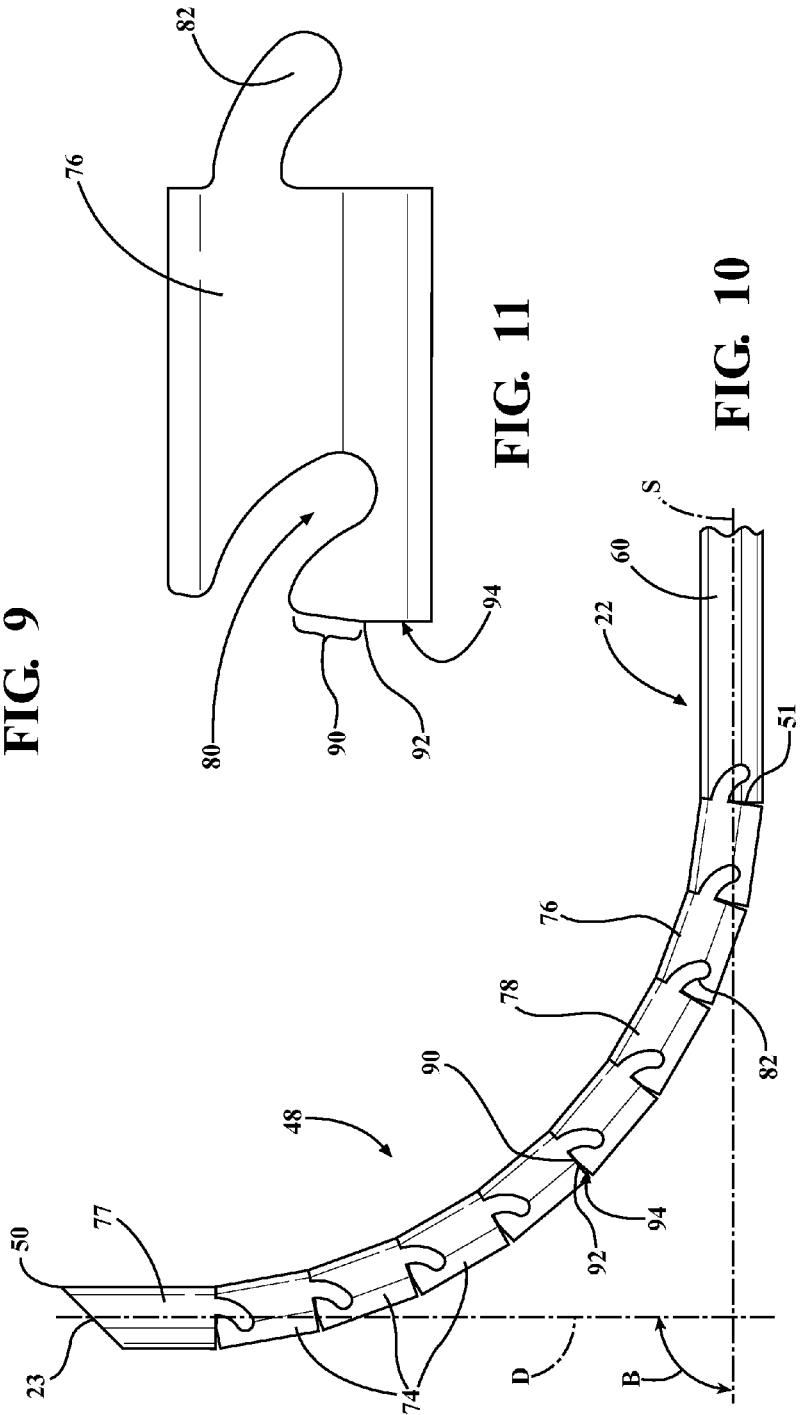

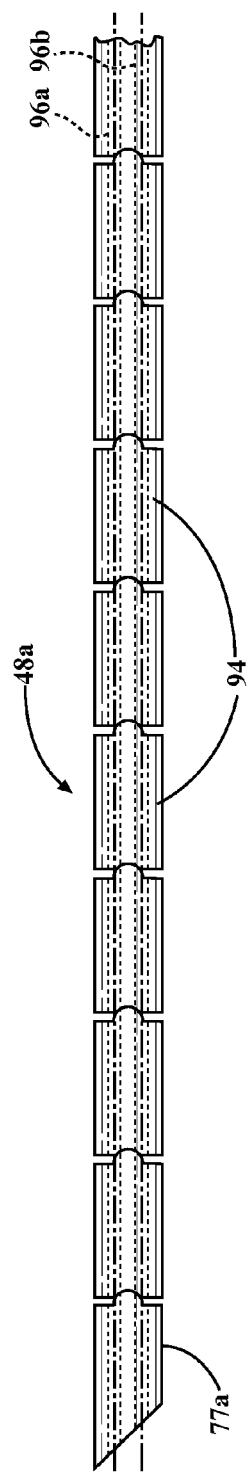
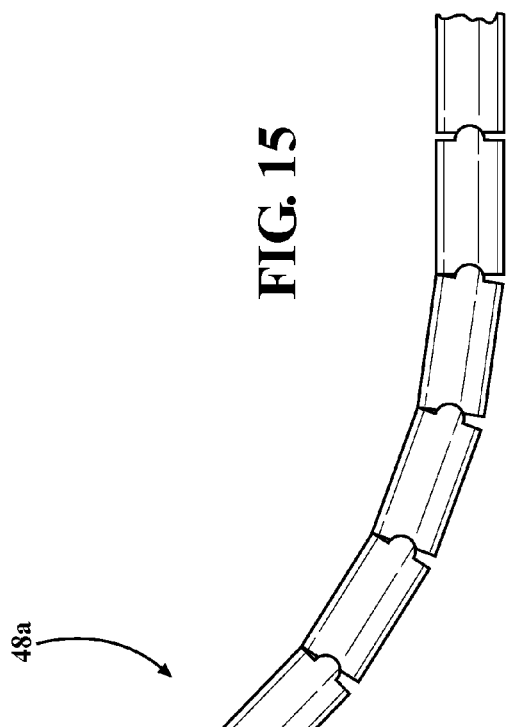
FIG. 14
FIG. 15

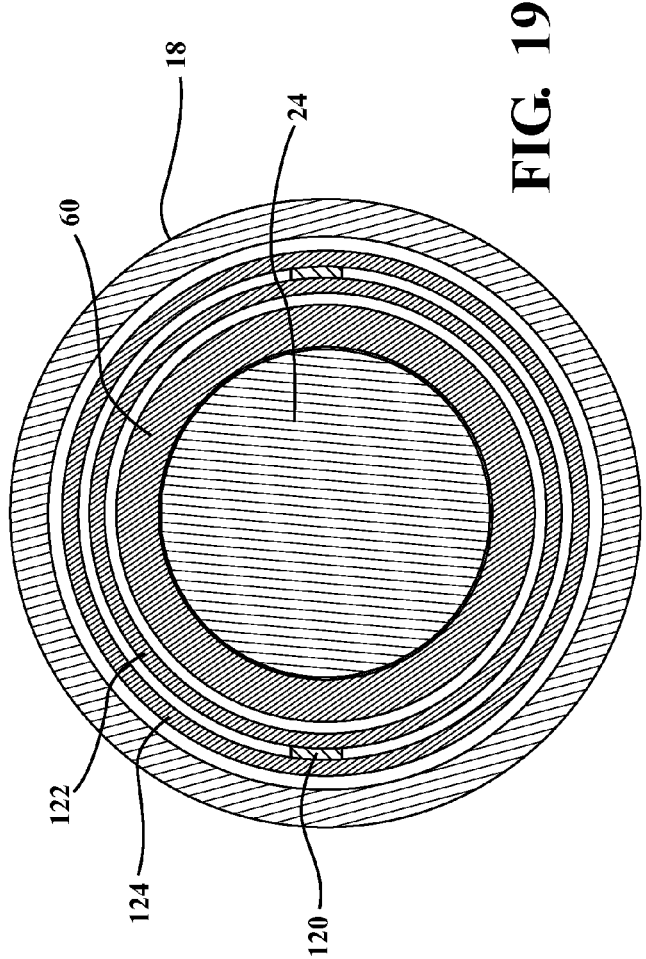
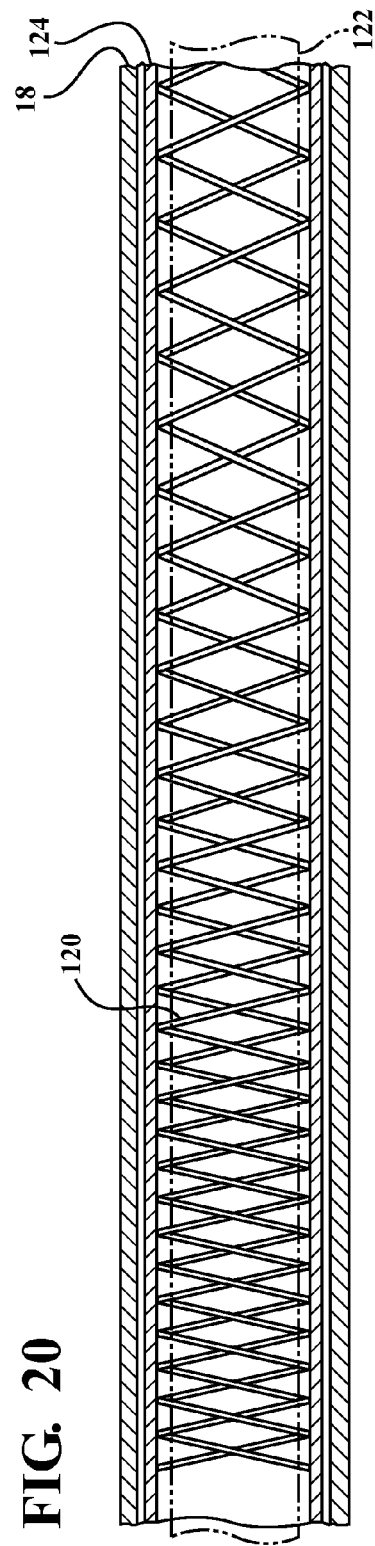
FIG. 19
FIG. 20

SYSTEMS AND METHODS FOR OFF-AXIS TISSUE MANIPULATION

CROSS-REFERENCE TO RELATED APPLICATIONS

This application claims priority to U.S. Provisional Patent Application No. 61/662,223, filed on Jun. 20, 2012, which is hereby incorporated by reference in its entirety.

FIELD OF THE INVENTION

The present invention generally relates to systems and methods for manipulating tissue. More particularly, the systems and method involve off-axis tissue manipulation.

BACKGROUND OF THE INVENTION

Osteoporosis, trauma, tumors, stress and degenerative wear can cause defects in vertebrae for which surgical intervention is useful. One of the more common ailments is vertebral compression fractures. These and other pathologies of the vertebrae are often treated with implants that can stabilize a vertebra, restore vertebra height, or to relieve pain and restore natural movement of the spinal column. One form of treatment for a vertebra is kyphoplasty. Another form of treatment is vertebroplasty.

In a typical kyphoplasty procedure, an access cannula is first placed through the skin into a vertebra to provide access inside the vertebra for other tools. Due to the location of delicate spinal structures, the access cannula is carefully placed along traditional straight access paths such as a transpedicular approach to the vertebra. Once the access cannula is in position, an expandable structure is inserted through the access cannula and into the vertebra. The expandable structure is then expanded to compress cancellous bone within the vertebra. As a result, a cavity is created in the vertebra. Once the cavity is created, hardenable material is implanted into the cavity to stabilize the vertebra. In vertebroplasty procedures, the hardenable material is implanted into the vertebra without the use of an expandable structure, i.e., the hardenable material is implanted directly into the cancellous bone in the vertebra.

Often, however, treatment of the vertebra along a straight access path is difficult due to the location of the target treatment site. In some cases, treatment requires placement of the hardenable material at a location offset from the straight access path provided by the access cannula, e.g., more centrally located in the vertebra. In prior art methods, when faced with this situation, two access cannulae are placed along two straight access paths using two transpedicular approaches (i.e., bi-pedicular) and the kyphoplasty or vertebroplasty is carried out through both access cannulae. For instance, if performing kyphoplasty, two expandable structures are separately deployed into the vertebra through the access cannulae and two cavities are created and filled with hardenable material to provide the needed treatment.

Alternatively, some prior art tools are formed of shape memory material and have pre-formed bends or curves at their distal end, such as curved needles, to access off-axis locations in tissue. The pre-formed bends typically have fixed degrees of curvature. Depending on the surgery to be conducted, the pre-fixed degrees of curvature of these tools may be unable to manipulate tissue at the target site in the manner desired, and therefore, lack versatility. In other words, because the prior art tools are pre-formed, they have a predetermined degree of curvature which does not allow their use in all types of surgical applications.

Therefore, there remains a need for systems and methods that utilize minimally invasive procedures for manipulating tissue in a position that is off-axis from traditional straight axis approaches.

SUMMARY OF THE INVENTION AND ADVANTAGES

A system for manipulating tissue is provided. The system comprises an access cannula for positioning in the tissue and a steerable assembly. The steerable assembly includes a steerable instrument and a deformable conduit. The steerable instrument is capable of being removably and at least partially, disposed, in the deformable conduit. The steerable instrument comprises a control element and a deflectable portion operatively connected to the control element. The steerable instrument is capable of assuming at least a substantially straight configuration and a curved configuration when the deflectable portion protrudes from the distal end of the access cannula. The steerable instrument is actuatable to move the deflectable portion away from the longitudinal axis of the access cannula in order to deform the deformable conduit so that the deformable conduit occupies a deformed position.

A system comprising an access cannula and a steerable instrument having a deflectable portion with a plurality of movable segments is also provided. The plurality of movable segments is collectively capable of assuming at least a substantially straight configuration and a curved configuration when the deflectable portion protrudes from a distal end of the access cannula. The steerable instrument is actuatable to move the deflectable portion away from the longitudinal axis of the access cannula in order to deform the deformable conduit so that the deformable conduit occupies a deformed position.

A surgical method for manipulating tissue is further provided. The surgical method utilizes an access cannula and a steerable assembly. The steerable assembly comprises a steerable instrument and a deformable conduit. The steerable instrument is removably, and at least partially, disposed within the deformable conduit. The steerable instrument comprises a control element and a deflectable portion operatively connected to the control element. The deflectable portion is capable of assuming at least a substantially straight configuration and a curved configuration when the deflectable portion protrudes from the distal end of the access cannula. The access cannula is positioned in the tissue to be manipulated. The steerable assembly is directed through the access cannula such that at least the portion of the steerable assembly protrudes from the distal end of the access cannula. The steerable instrument is actuated while the steerable instrument is at least partially disposed within the deformable conduit to move the deflectable portion of the steerable instrument and a distal end of the deformable conduit away from the longitudinal axis of the access cannula such that the deformable conduit occupies a deformed position. The steerable instrument is retracted from the deformable conduit after the deformable conduit occupies the deformed position.

Patient anatomy presents certain challenges for offset tissue manipulation that are not adequately addressed by existing systems and methods for off-axis procedures. Tissue density may vary greatly between patients, from soft tissues outside of bone, to soft cancellous bone in an osteoporotic fracture, to much harder bone in fractures from traumatic injury or metastatic disease. Vertebrae for example will also vary greatly in shape depending on the level being treated. Pedicles and vertebral bodies progressively decrease in size from lower lumbar to upper thoracic, and the pedicle angle (as measured from a sagittal plane) varies from approximately 45° at L5 to approximately 0° at T12. The disclosed systems and methods for off-axis procedures possess the combination of properties to allow for use in both a wide range of tissue densities and varying anatomical shapes.

These systems and methods advantageously allow a clinician to access off-axis locations offset from a straight access path without utilizing multiple access paths. However, it should be appreciated that multiple access paths could be used in some situations. Furthermore, the systems and methods may allow a clinician to adjust the angle the curvature to a plurality of different angles of curvature between a substantially straight configuration and a curved configuration such that a single tool may be suitable for a wide range of surgical conditions. This increases procedural flexibility while minimizing the challenges associated with multiple access cannula insertions.

BRIEF DESCRIPTION OF THE DRAWINGS

Advantages of the present invention will be readily appreciated by reference to the following detailed description when considered in connection with the accompanying drawings.

FIG. 7A is a cross-sectional view of one embodiment of a steerable instrument with a ratchet assembly;

FIG. 9 is a top view of a deflectable portion of the steerable instrument in a substantially straight configuration comprising a plurality of interlocking links;

FIG. 10 is a top view of the deflectable portion of the steerable instrument in a curved configuration comprising the plurality of interlocking links;

FIG. 11 is a top view of a first link of the plurality of interlocking links of FIGS. 9 and 10;

FIG. 14 is a top view of an alternative deflectable portion of the steerable instrument in a substantially straight configuration comprising a plurality of multi-directional links; and FIG. 15 is a top view of the alternative deflectable portion of the steerable instrument in a curved configuration comprising the plurality of multi-directional links;

FIG. 19 is a cross-sectional view of FIG. 18;

FIG. 20 is a longitudinal cross-sectional view of the deformable conduit of FIG. 18;

DETAILED DESCRIPTION OF THE INVENTION

The systems and methods described herein may be used for a number of different procedures including, for example, kyphoplasty, vertebroplasty, and other bone augmentation procedures, including procedures in which an implant or other treatment is delivered to a tissue location, as well as possibly to compact, displace, remove or aspirate material from a tissue site. The systems and methods may also be used to treat tissue in other regions of the body, such as soft tissue or skin. The system may furthermore be used to deliver energy to tissue using radiofrequency ablation devices and techniques.

In one embodiment, the present systems and methods advantageously allow off-axis kyphoplasty and vertebroplasty to avoid the expense and challenges involved in bi-pedicular access of the vertebra. By allowing a clinician to access cancellous bone radially offset from the longitudinal axis of an access cannula, the clinician is able to access volumes of the vertebra which are not accessible using conventional kyphoplasty and vertebroplasty approaches.

The vertebra 10 includes two pedicles 12, cortical bone 14, and cancellous bone 16, along with other bodily material (e.g., blood, marrow, and soft tissue). As a point of reference, the systems and methods of the present disclosure may be suitable or readily adapted by those of ordinary skill in the art for accessing a variety of bone sites. Thus, although the vertebra 10 is illustrated, it is to be understood that other bone sites may be accessed and treated by the systems and methods (e.g., pelvis, long bones, ribs, and sacrum).

Figure 1:
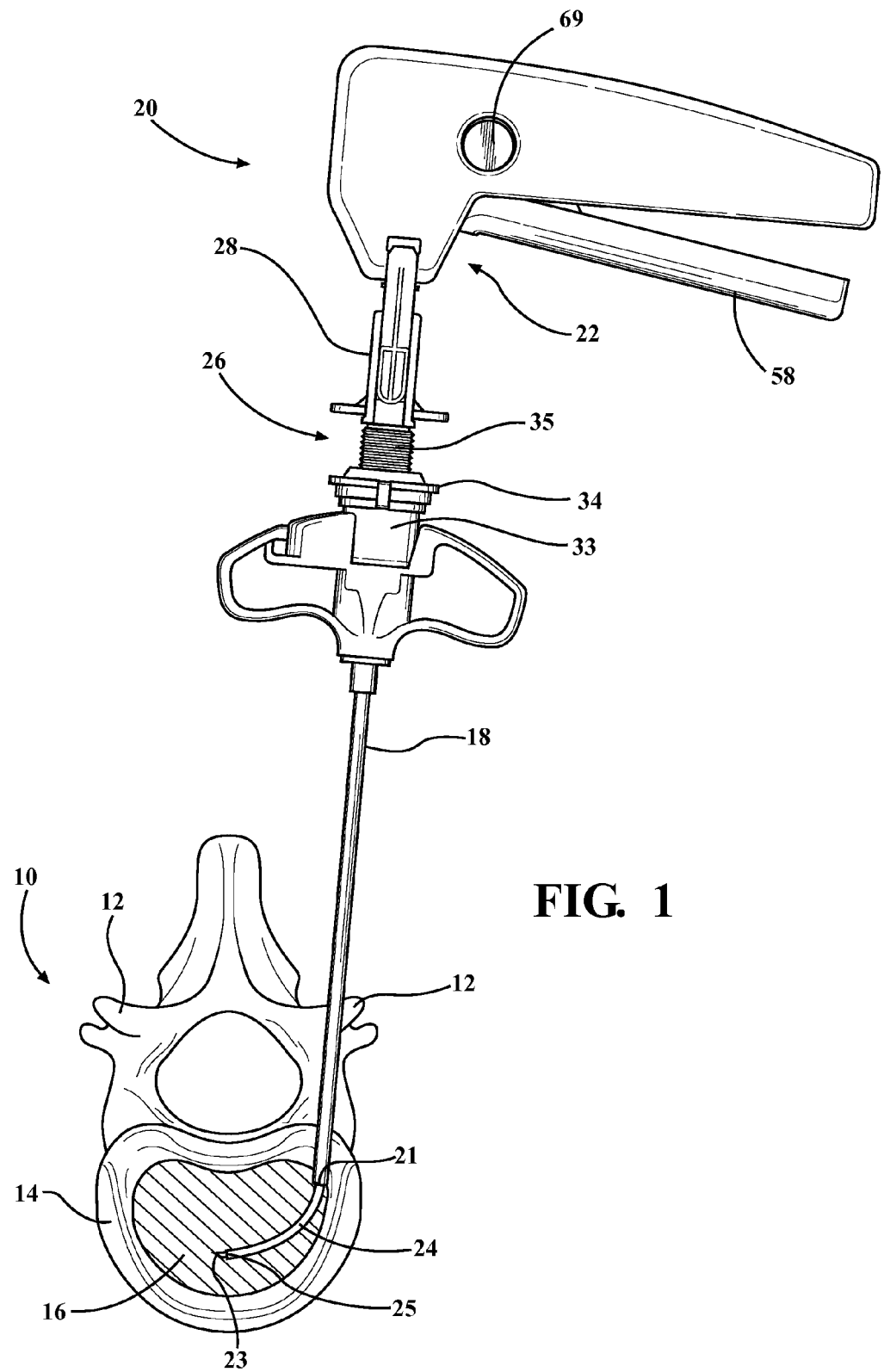
FIG. 1 is a top view of a steerable assembly positioned in an access cannula in accordance with one embodiment of the present invention.

Referring to FIG. 1, the system comprises an access cannula 18 and a steerable assembly 20. The steerable assembly 20 comprises a steerable instrument 22 and a deformable conduit assembly 26 coupled to the steerable instrument 22 via a hub 28. The deformable conduit assembly 26 includes a deformable conduit 24. The steerable instrument 22 is capable of being removably and at least partially disposed in the deformable conduit 24.

The steerable instrument 22 is actuatable in order to deform the deformable conduit 24 into a deformed configuration from a normally straight configuration. One example of the deformed configuration is shown in FIG. 1. By placing the deformable conduit 24 into the deformed configuration, other instruments, materials, etc. can be placed in the vertebra 10 through the deformable conduit 24 at a location that is offset from a longitudinal, straight access path created by the access cannula 18.

Figures 2, 3:
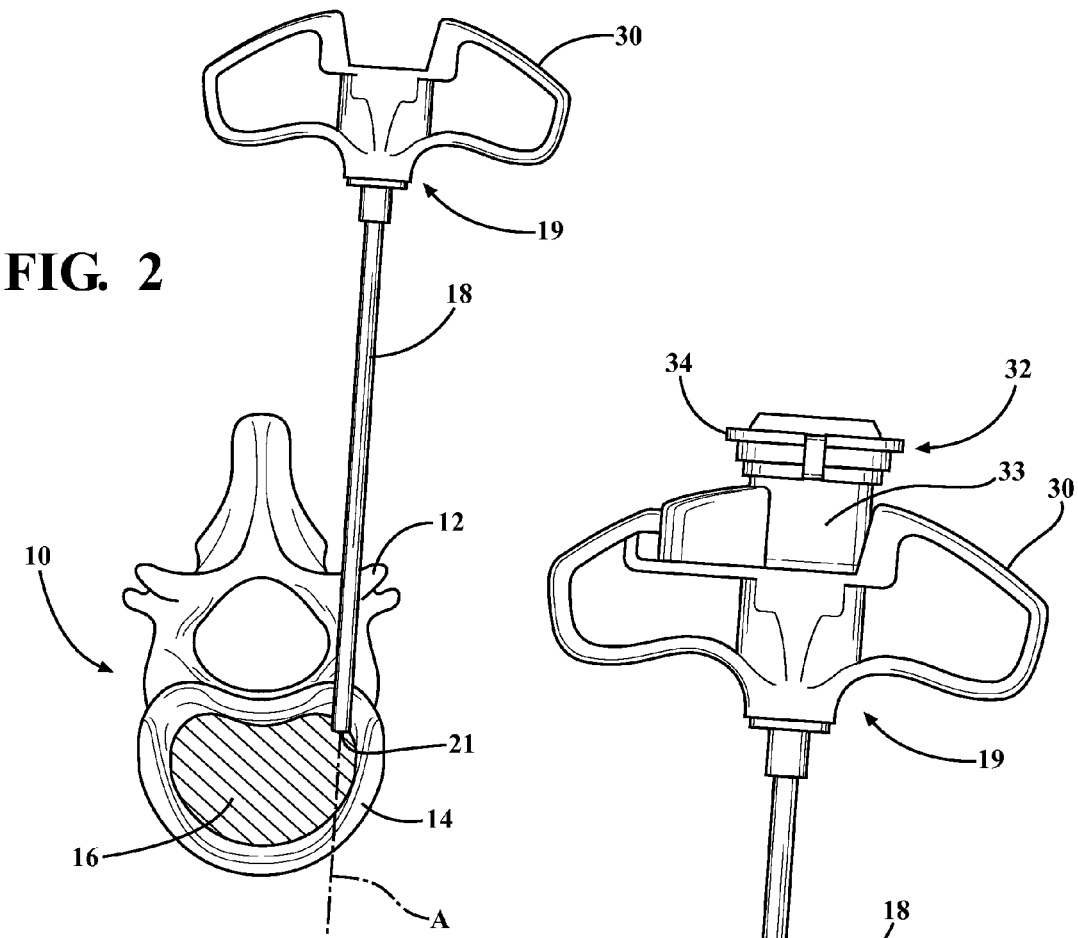
FIG. 2 is a top view of an access cannula positioned in a vertebra.
FIG. 3 is a top view of the access cannula of FIGS. 1 and 2 with a cannula adapter positioned thereon.
Figure 4:
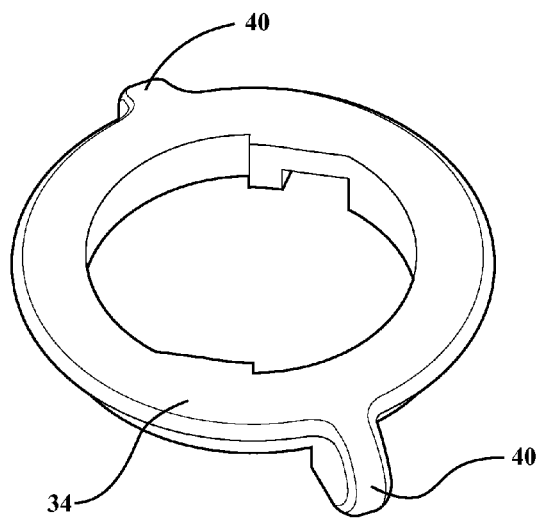
FIG. 4 is a perspective view of a lock ring in accordance with one embodiment.

Referring to FIGS. 2 and 3, the access cannula 18 is configured for being positioned and placed in the tissue at the target site along a straight, longitudinal access path using a stylet (not shown) coaxially disposed in the access cannula 18. The access cannula 18 defines a lumen about a longitudinal axis A to provide access into the internal portion of the vertebra 10. The access cannula 18 comprises a proximal end 19 configured for penetrating hard tissue and a distal end 21 configured for manipulation. The lumen is dimensioned to allow other instruments, such as the steerable instrument 22 and the deformable conduit 24 to pass there through. In certain embodiments, the access cannula 18 may range in size from 6 to 13 gauge.

Figure 8:
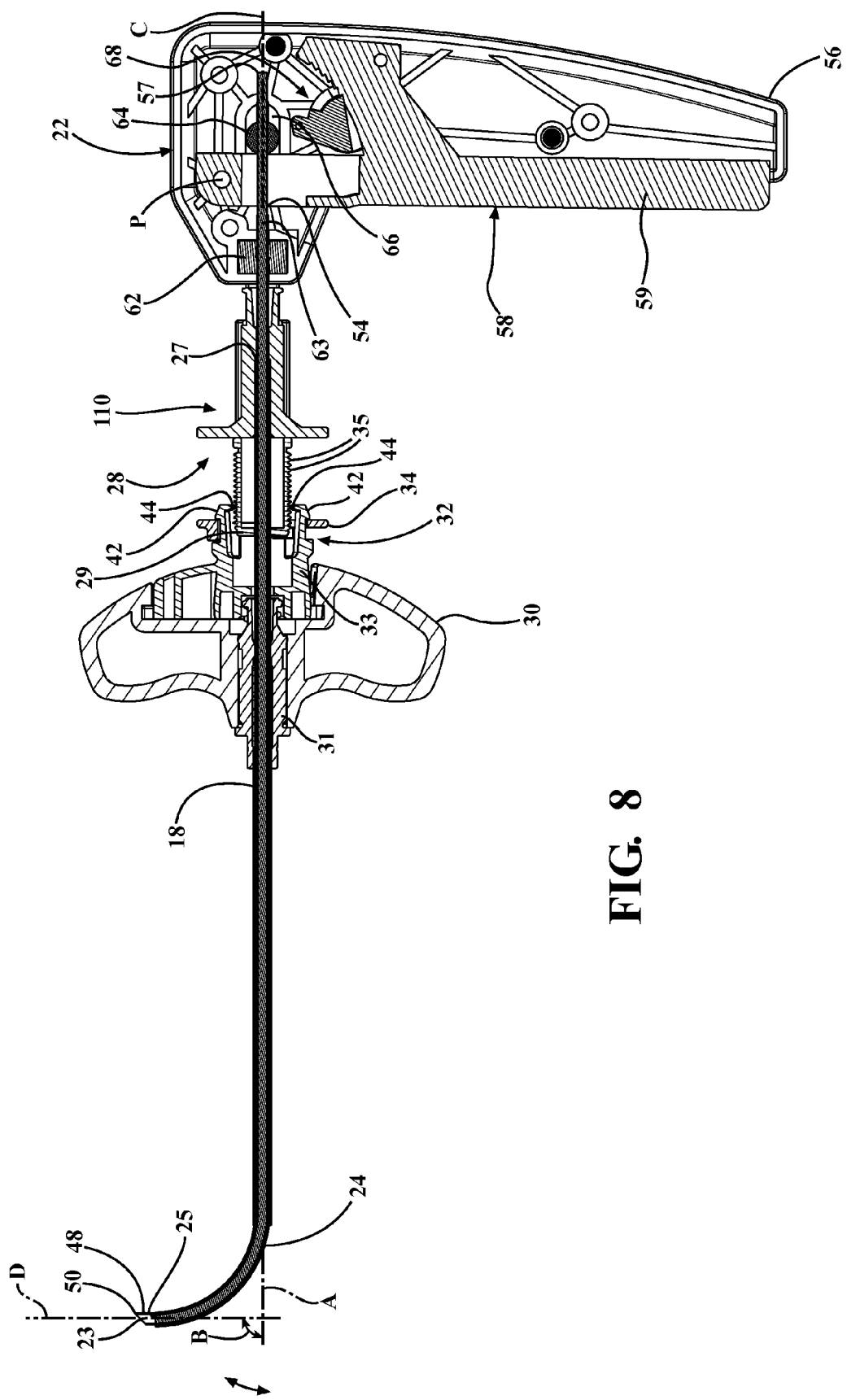
FIG. 8 is a cross-sectional view of the steerable assembly including the steerable instrument and the deformable conduit assembly positioned in the access cannula.

A cannula handle 30, shown in FIG. 8, may be attached to the proximal end 19 of the access cannula 18 for longitudinally or rotationally manipulating the access cannula 18. The access cannula 18 preferably comprises surgical grade stainless steel, but may be made of known equivalent materials that are both biocompatible and substantially non-compliant, such as other medical alloys and plastics.

A cannula hub 31 may be fixedly mounted to the proximal end 19 of the access cannula 18 to prevent the access cannula 18 from moving relative to the cannula handle 30. The cannula hub 31 may be molded onto the proximal end 19 of the access cannula 18 or fixed thereto in other conventional ways. Likewise, the cannula hub 31 may be fixed to the cannula handle 30 by conventional methods such as adhesive, press fit, or the like.

Referring to FIG. 3, in some embodiments, a cannula adapter 32 is provided adjacent to the cannula handle 30. The cannula adapter 32 is rotationally and axially locked to the access cannula 18 using conventional methods (via cannula handle 30). The cannula adapter 32 may simply act as an extension of the cannula handle 30. The cannula adapter 32 is configured to interact with the hub 28 of the deformable conduit assembly 26. For example, the cannula adapter 32 may provide for releasably axially fixed attachment to the hub 28, to prevent the access cannula 18 from moving in a longitudinal direction relative to the hub 28. The cannula adapter 32 may be integrally formed with, or otherwise fixed to, the access cannula 18, or the cannula handle 30, or may be releasably attached to the access cannula 18 or cannula handle 30. Axially fixing the hub 28 relative to the access cannula 18, which is fixed relative to the vertebra 10, minimizes the potential for disruption of the deformable conduit 24 while the clinician performs other steps, such as retraction or withdrawal of the steerable instrument 22, or delivering an implant or treatment through the deformable conduit 24.

Referring to FIGS. 3-6, the cannula adapter 32 comprises a body 33 and lock ring 34 rotatable relative to the body 33. Referring back to FIG. 1, the lock ring 34 is actuated by a clinician to lock the hub 28 axially in place with respect to the access cannula 18, while allowing the hub 28 to rotate relative to the access cannula 18. This allows the clinician to adjust the planar orientation of the steering instrument 20 while remaining axially locked in place. The lock ring 34 is configured to urge the cannula adapter 32 to engage a grooved section of the hub 28. The grooved section of the hub 28 may comprise one or more spaced grooves 35.

Figures 5, 6:
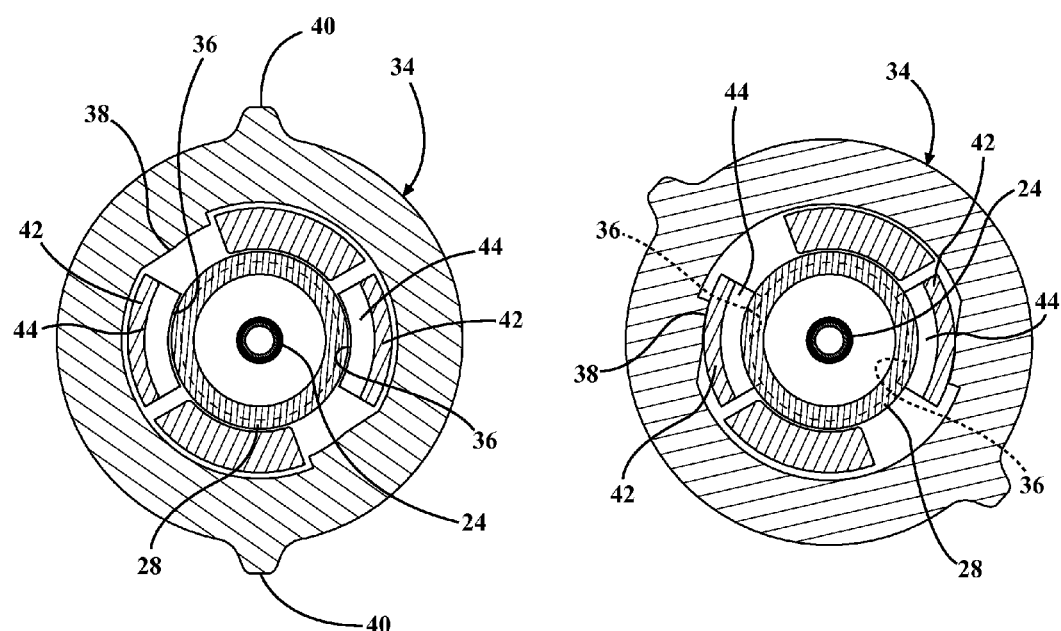
FIG. 5 is a cross-sectional view of the lock ring in an unlocked position with respect to a hub of a deformable conduit assembly.
FIG. 6 is a cross-sectional view of the lock ring in a locked position with respect to the hub of the deformable conduit assembly.

Referring to FIGS. 5 and 6, in one embodiment, the lock ring 34 comprises at least one locking ramp 38. The lock ring 34 also may comprise one or more ring tabs 40, for being engaged by a clinician to rotate the lock ring 34. As the lock ring 34 is rotated by the clinician, the locking ramp 38 engages one or more cantilever arms 42 of the body 33, moving the cantilever arms 42 inwards towards the center of the lock ring 34. As the lock ring 34 is in a fully rotated position (see FIG. 6), at least one locking surface 36 of the cantilever arms 42 engages one of the spaced grooves 35 in the grooved section of the hub 28, to prevent axial movement of the hub 28 relative to the access cannula 18. The cantilever arms 42 may comprise at least one cantilever tooth 44 possessing the locking surface 36 dimensioned to engage one or more of the spaced grooves 35 among the plurality of axially spaced grooves 35 located on the grooved section of the hub 28.

The lock ring 34 may be configured to lock after rotation of less than 90, less than 60, less than 45, or less than 30, degrees of rotation relative to the access cannula 18. In one embodiment, the lock ring 34 may comprise a recess that interacts with a stop member disposed on the cannula adapter 32. After locking, the stop member may protrude into the recess of the lock ring 34 and prevent the lock ring 34 from rotating more than a predetermined amount in either direction. During operation, as the clinician rotates the lock ring 34 to axially lock the access cannula 18 to the hub 28, the stop member eventually engages a surface forming the recess and prevents the clinician from rotating the lock ring 34 any further. Similarly, as the clinician reversibly rotates the lock ring 34 to release the hub 28, the stop member eventually engages an opposing surface forming the recess and prevents the clinician from rotating the lock ring 34 any further. Alternative stop mechanisms are also contemplated which function to prevent over-rotation of the lock ring 34 relative to the cannula adapter 32.

Referring again to FIG. 1, the system also comprises the steerable instrument 22. The steerable instrument 22 has a length sufficient to extend beyond the distal end 25 of the deformable conduit 24 and the distal end 21 of the access cannula 18. The steerable instrument 22 also has a diameter sufficient to be slidably disposed in a lumen of the deformable conduit 24.

Figure 7:
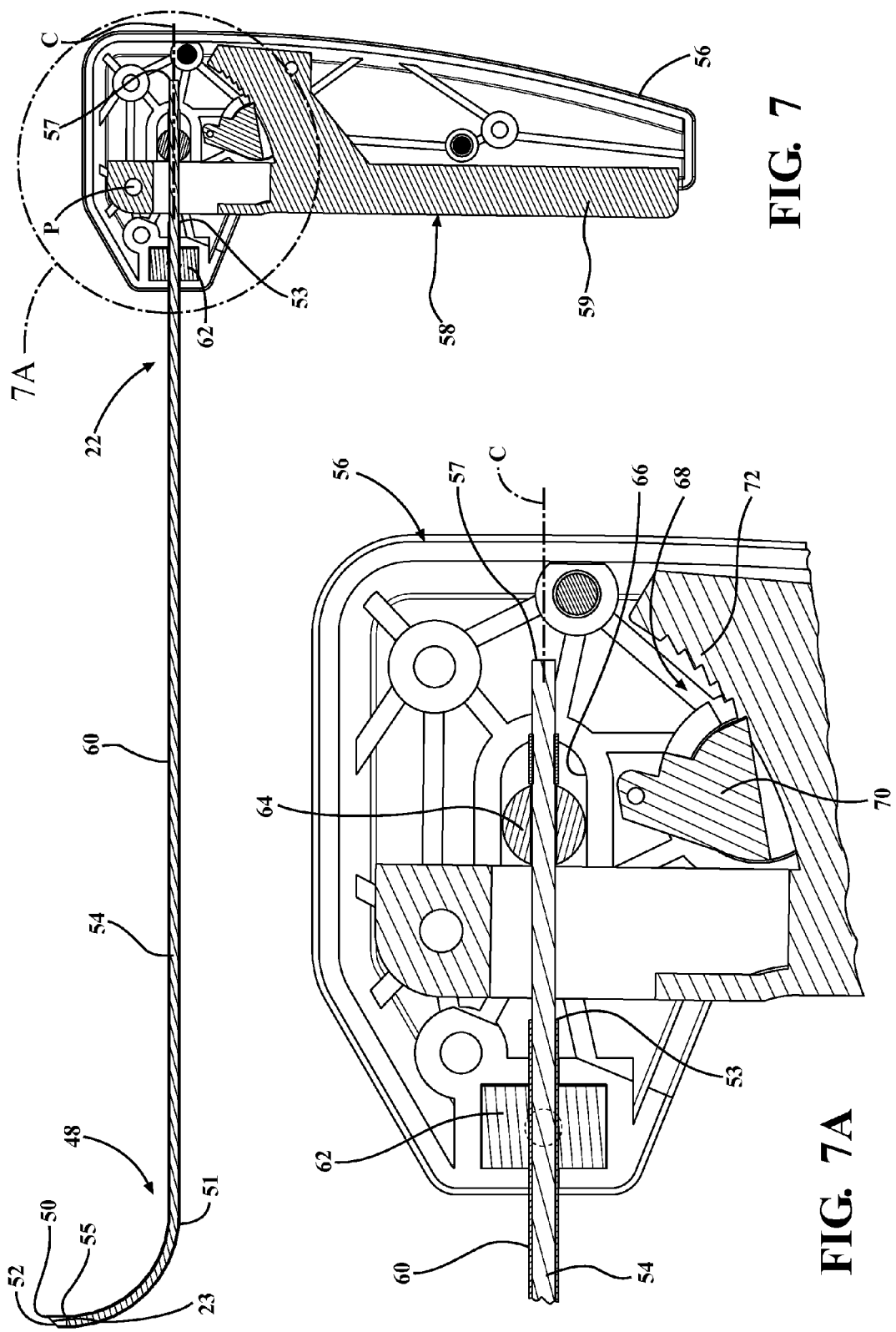
FIG. 7 is a cross-sectional view of a steerable instrument in accordance with one embodiment.

Referring to FIGS. 7, 7A, and 8, the steerable instrument 22 comprises a deflectable portion 48 capable of assuming at least a substantially straight configuration and a curved configuration. The steerable instrument 22 is actuated to assume the curved configuration when the deflectable portion 48 protrudes from the distal end 21 of the access cannula 18. A distal end 23 of the steerable instrument 22 may be aligned with the distal end 25 of the deformable conduit 24, or may protrude beyond the distal end 25 of the deformable conduit 24. In some embodiments, the distal end 23 of the steerable instrument 22 extends beyond the distal end 25 of the deformable conduit 24 by at least 0.1, 0.5, 1, or 2, mm.

The substantially straight configuration of the deflectable portion 48 is substantially coaxial with the longitudinal axis A of the access cannula 18 when the steerable instrument 22 is at least partially disposed within the access cannula 18. The phrase "substantially straight" refers to those configurations of the deflectable portion 48 where the distal end 23 of the steerable instrument is angled away from the longitudinal axis A of the access cannula 18 at an angle of curvature B of less than 15, 10, 5, 3, or 1, degrees.

Referring to FIGS. 7 and 8, the curved configuration of the steerable instrument 22 results in the distal end 23 of the deflectable portion 48 of the steerable instrument 22 being radially offset from the longitudinal axis A of the access cannula 18. The distal end 23 of the deflectable portion 48 may be deflected through angles of curvature B ranging from about 10 degrees to 25, 35, 60, 90, 120, or 150, degrees, or more, relative to the longitudinal axis A of the access cannula 18. In FIG. 8, the distal end 23 of the deflectable portion 48 is shown deflected by an angle of curvature B of approximately 90 degrees relative to the longitudinal axis A of the access cannula 18. In other words, the steerable instrument 22 is actuatable and capable of assuming the substantially straight configuration, a fully actuated curved position, and any desired position in between.

In some embodiments, the deflectable portion 48 may be actuated into a plurality of different predetermined radially offset positions with each of the plurality of different predetermined radially offset positions having an angle of curvature B, based on the angle the distal end 23 of the steerable instrument 22 extends from the longitudinal axis A of the access cannula 18. In one embodiment, the deflectable portion 48 may be capable of curving in a single plane of motion. Alternatively, the deflectable portion 48 may be capable of curving in multiple planes of motion.

When the steerable instrument 22 is actuated, the angle of curvature B of the distal end 23 of the deflectable portion 48 may be gradually manipulated until the desired angle of curvature B is achieved. In other words, the deflectable portion 48 of the single steerable instrument 22 is capable of assuming a variety of different angles of curvature B, based on the extent of actuation of the steerable instrument 22. Furthermore, the radius of curvature can be determined by extending the deformable conduit 24 and/or the steerable instrument 22 through the distal end 21 of the access cannula to a greater degree with respect to one another.

Alternatively, the steerable instrument 22 may be pre-tensioned such that upon emergence from the distal end 21 of the access cannula 18, the deflectable portion 48 immediately assumes the angle of curvature B associated with the extent of pre-tensioning.

The angle of curvature B of the deflectable portion 48 can be observed fluoroscopically, and/or by printed or other indicia associated with the steerable instrument 22. The deformable conduit 24 may further include indicia visible under intraoperative imaging to assist in visualizing the deformable conduit 24 during placement. Such indicia may include radiopaque elements, such as metal reinforcement, filler material (e.g., barium sulfate) in the polymeric components, and/or one or more radiopaque markers (not shown). The curvature of the deflectable portion 48 allows the distal end 23 of the steerable instrument 22 to contact tissue which is radially offset from the longitudinal axis A of the access cannula 18.

Referring again to FIG. 7, the steerable instrument 22 may comprise a tip 50 located on the distal end 23 of the deflectable portion 48. The tip 50 may be sharp, rounded, or blunt. The tip 50 may optionally include a port 52 which allows the implant, such as a hardenable material, to be injected into hard tissue through the steerable instrument 22. Alternatively, the tip 50 may be occluded such that no material can pass therethrough.

Referring to FIG. 7A, the steerable instrument 22 includes a control element 54. The deflectable portion 48 is operatively connected to the control element 54. In the embodiment shown, the distal end 55 of the control element 54 is connected to the deflectable portion 48. The deflection of the deflectable portion 48 of the steerable instrument 22 is accomplished by exerting tension on the control element 54, or by moving the control element 54 in a longitudinal direction along a control axis C of the steerable instrument 22. In one embodiment, as the steerable instrument 22 is actuated, the control element 54 is moved along the control axis C to control the angle of curvature B of the deflectable portion 48.

Referring to FIG. 8, in one embodiment, the control element 54 operates in a plurality of tension modes including an operating tension mode that enables the deflectable portion 48 to place the deformable conduit 24 in the deformed position and a slack tension mode to allow withdrawal of the deflectable portion 48 of the steerable instrument 22 from the deformable conduit 24 without substantially displacing the deformed position of the deformable conduit 24 once deformation is complete. The phrase "substantially displacing" is intended to refer to displacement of the distal end 25 of the deformable conduit 24, after the deformable conduit 24 maintains the deformed position, of more than 0, more than 0.1, more than 0.3, more than 0.5, more than 0.75, more than 1, or more than 3, cm, in a lateral direction relative to the position of the distal end 25 of the deformable conduit 24 before retraction. In the operating tension mode, at least some tension is placed on the control element 54 such that the deflectable portion 48 is prevented from returning to a non-actuated position (e.g., straight). Although tension is mentioned, it will be understood that a plurality of actuation modes could also be referenced, such as a positively actuated mode and a non-actuated mode for embodiments where tension is not used to actuate the steerable instrument 22.

If the steerable instrument 22 is disposed outside the lumen of the deformable conduit 24 and the control element 54 is in the slack tension mode, the steerable instrument 22 assumes a substantially straight configuration. The slack tension mode allows the deflectable portion 48 to move freely, which allows easy retraction of the steerable instrument 22 through the deformable conduit 24. In the slack tension mode, the steerable instrument 22 exerts substantially zero lateral force on the deformable conduit 24 as the steerable instrument 22 is withdrawn from the deformable conduit 24. This allows the steerable instrument 22 to be slidably removed from the deformable conduit 24 after the deformable conduit 24 is in the deformed position relative to the longitudinal axis A of the access cannula 18. In other words, when the steerable instrument 22 is operated in a slack tension mode, the deflectable portion 48 of the steerable instrument 22 becomes limp and exerts substantially no lateral force in any direction and is adapted to readily conform to the deformed position of the deformable conduit 24 without causing the deformable conduit 24 to be substantially displaced from the deformed position. This feature allows the deformable conduit 24 to maintain its position in softer tissues, such as osteoporotic bone, or tissues outside of bone.

In some embodiments, the control element 54 may comprise one or more wires, bands, rods, or cables, which are attached to the deflectable portion 48. The control elements 54 may be spaced axially apart along the length of the deflectable portion 48 to allow the distal end 23 of steerable instrument 22 to move through compound bending curves. In the embodiment shown, the control element 54 is a single cable or wire attached to the deflectable portion 48. The distal end of the control element 54 may be fastened to the distal end 23 of the deflectable portion 48 by welding, crimping, soldering, brazing, or other fastening technology.

Referring again to FIG. 8, the steerable instrument 22 may further comprise a steering handle 56, and/or a control surface 58. The steering handle 56 may allow the clinician to rotate the steerable instrument 22 relative to the access cannula 18 or the deformable conduit 24. The proximal end 57 of the control element 54 may be disposed in the steering handle 56. In one possible configuration, the control surface 58 may be at least partially disposed within the steering handle 56. The control surface 58 is operatively connected to the control element 54. Therefore, the control surface 58 may be manipulated by the clinician to cause the deflectable portion 48 of the steerable instrument 22 to occupy a position radially offset from the longitudinal axis A of the access cannula 18 and to assume a desired angle of curvature B. In other words, actuation of the control surface 58 may cause the deflectable portion 48 of the steerable instrument 22 to move away from the longitudinal axis A of the access cannula 18. In certain exemplary embodiments, actuating the steerable instrument 22 comprises manually engaging the control surface 58, to control the angle of curvature B of the deflectable portion 48. However, the control surface 58 may also be engaged using mechanized, electric, or automated devices.

The control surface 58 may allow for continuous and positive adjustment of the angle of curvature B of the deflectable portion 48 throughout the entire range of possible angles of curvature B. In other embodiments, the control surface 58 may be configured for stepwise adjustment of the curvature of the deflectable portion 48, to the plurality of possible angles of curvature B via a ratchet assembly 68. Alternatively, the control surface 58 may be configured to place the control element 54 in one or more of the plurality of tension modes described above.

The control surface 58 may comprise a thumbwheel, slider, button, trigger, rotatable knob, or combinations thereof, and may be actuated by rotating, pulling, sliding, squeezing, or pushing the control surface 58. The control surface 58 may be configured to allow for one-handed operation by a clinician.

Referring to FIG. 7A, the steerable instrument 22 further comprises a shaft 60 having a distal end 51 and a proximal end 53. The control element 54 resides within a lumen of the shaft 60, or may be provided external to the shaft 60. The proximal end 53 of the shaft 60 is may be disposed within the steering handle 56. The proximal end 53 of the shaft 60 is engaged by a mounting block 62 fixed to the steering handle 56 that maintains alignment of the shaft 60 within the steering handle 56. The proximal end 53 of the shaft 60 is fixed to the mounting block 62. In certain embodiments, the control element 54 passes through the shaft 60 and the proximal end of the control element 54 is operatively coupled to the control surface 58.

In the embodiment shown, the steering handle 56 further comprises a guide cylinder 64 having a hole disposed there through. The control element 54 passes through the hole in the guide cylinder 64. The proximal end 57 of the control element 54 is engaged by a crimp sleeve, weld, adhesive, or other fastening method to prevent the proximal end 57 of the control element 54 from being pulled back through the hole in the guide cylinder 64 during operation. A flexible member, such as a spring may be positioned to operably interact with both the control surface 58 and the control element 54 to control or limit the amount of force that the control surface 58 is able to apply to the control element 54.

The steering handle 56 defines a void 66. The guide cylinder 64 is slidably disposed in the void 66 to guide the guide cylinder 64 such that the guide cylinder 64 may move freely in a linear direction along the control axis C, substantially aligned with the shaft 60 but may not move transversely relative to the shaft 60 of the steerable instrument 22. In one specific embodiment, the control surface 58 is presented by a trigger 59, and the trigger 59 has a rear surface that engages the guide cylinder 64 as the trigger 59 pivots about the pivot P, which during actuation, induces tension in the control element 54. The trigger 59 may be biased towards the slack tension mode by virtue of a trigger spring (not shown) or other device operable to bias the trigger in the non-actuated position. In certain embodiments, the control surface 58 is configured to apply force to the control element in only one direction of actuation. This allows the control surface 58 (and the control element 54) to return to a rest position while remaining in slack mode, and prevents forces from other elements, such as springs, gravity, and inadvertent movement of the control surface 58, from affecting the position of the deformable conduit 24.

The ratchet assembly 68 interacts with the trigger 59 to selectively retain the deflectable portion 48 in one of the plurality of tension modes or angles of curvature B. Alternatively, or in addition to the ratchet assembly 68 being operatively connected to the control element 54, the ratchet assembly 68 may be operatively connected to the control surface 58. The ratchet assembly 68 may be selectively disengaged by touching a release button 69 or other device, such that the control element 54 may move freely between a non-actuated and an actuated position.

The ratchet assembly 68 may be disposed at least partially within the steering handle 56. The ratchet assembly 68 may comprise a pawl 70 disposed within the steering handle 56 and a ratcheting member 72. The ratcheting member 72 may comprise a plurality of teeth that are capable of being engaged by the pawl 70. The pawl 70 may include one or more teeth which correspond to the teeth of the ratcheting member 72. The ratchet assembly 68 may further comprise a mount to orient the ratcheting member 72 or pawl 70 such that engagement of the ratchet assembly 68 places the pawl 70 into operative position with respect to the ratcheting member 72. In such embodiments, when the control element 54 is being actuated, the pawl 70 slides up over the edges of the trigger teeth of the ratcheting member 72. When the control element 54 is no longer being actuated, the pawl 70 will engage one of the plurality of teeth of the ratcheting member 72 and prevent the control element 54 from returning to the non-actuated configuration until released by pressing release button 69. Other configurations of the ratchet assembly 68 that are sufficient to selectively retain the deflectable portion 48 in one of the plurality of tension modes or curvature positions are also contemplated, such as a friction-based mechanism that selective retains the control element 54 in one of a plurality of frictionally engaged positions.

Referring to FIGS. 9-15, in one or more embodiments, the deflectable portion 48 of the steerable instrument 22 comprises a plurality of movable segments collectively capable of assuming at least the substantially straight configuration and the curved configuration. The size, shape, and/or spacing of the movable segments may affect the radius, angle of curvature, and/or limits of deflection for the deflectable portion 48 of the steerable instrument 22. The plurality of movable segments may comprise a plurality of interlocking and individual links 74. The phrase "individual links" refers to distinct and discrete members.

The plurality of individual links 74 allow the steerable instrument 22 to possess the slack mode, which enables withdrawal and retraction of the steering instrument 22 without substantially displacing the deformable conduit 24 from the deformed position. Furthermore, in one embodiment, the plurality of individual links 74 are in an unstrained state when the deflectable portion 48 assumes the substantially straight configuration. The unstrained state refers to a condition of the deflectable portion experiencing less than 3, 2.5, 2, 1.5, 1, or 0.5% strain. As a result, the clinician is not required to apply force to the control element 54 to straighten the deflectable portion 48 to the substantially straight configuration.

The plurality of individual links 74, shaft 60 and/or control element 54 are capable of being actuated with less than 3, 2.5, 2, 1.5, 1, or 0.5% strain, which allows the steerable instrument 22 to be actuated multiple times without inducing fatigue of the individual links 74 and premature failure. Furthermore, the plurality of individual links 74 may be actuated to a fully-actuated position without any of the plurality of individual links 74, the control element 54, or the shaft 60 undergoing permanent deformation.

Referring to FIGS. 9-13, the plurality of individual links 74 comprises at least one first link 76 and at least one second link 78. The distal end of the first link 76 engages a proximal end of the second link 76. Referring to FIG. 9, a plurality of the first links 76 and a plurality of the second links 78 may be included to form the deflectable portion 48. In the embodiment shown, the first and second links 76, 78 are identical in configuration.

In the substantially straight configuration, each link of the deflectable portion 48 is substantially co-axial with the adjacent link. In the embodiment shown, a distal link 77 is provided to form the distal end 23 of the deflectable portion 48 and the shaft 60 is configured to receive one of the links 76, 78.

Each of the plurality of links 74 may be hollow to allow the control element 54 to pass therethrough. The distal end 55 of the control element 54 may be welded or otherwise fastened on an interior surface of the distal link 77, or another link adjacent thereto. The actuation of the control element 54 may urge the distal link 77 in a proximal direction, which results in the curvature of the deflectable portion 48, and the articulation of the remaining links. In some embodiments, the control element 54 is only attached to the distal link 77 and is not attached to the remaining links. However, in other embodiments, the control element 54 may be attached to two or more of the plurality of links 74. In the embodiments shown, nine links 74, 77 are shown with each adding 10 degrees deflection from shaft axis S to provide an angle of curvature B of 90 degrees for the deflectable portion 48. The angle of curvature B, as shown in FIG. 10 can be measured between a central shaft axis S of shaft 60 and a central distal axis D of distal link 77.

Figure 13:
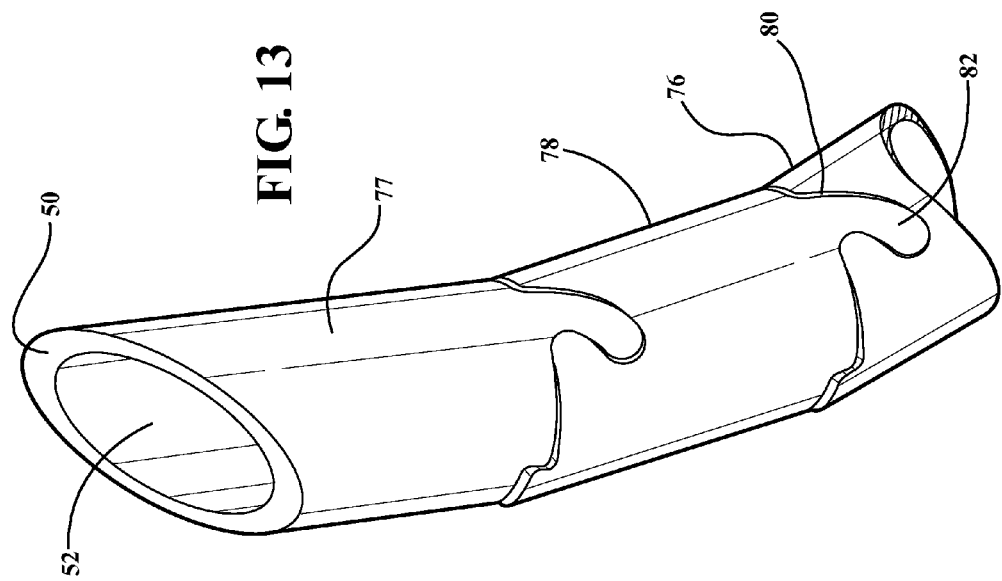
FIG. 13 is a perspective view of a distal end of the steerable instrument without the control element in place.

Referring to FIGS. 10 and 13, the distal end of each of the link 76, 78 comprises at least one slot 80 and the proximal end of each link 76, 78 comprises at least one follower 82. In the embodiment shown, each of links 76, 78 have two slots 80 and two followers 82. The followers 82 are configured to be movably disposed within the slots 80 of an adjacent link. The followers 82 and the slots 80 are arcuate in shape in some embodiments. The slots 80 may comprise an open-end and a closed end. In the actuated mode, the followers 82 of one link may touch the closed ends of the slots 80 of an adjacent link (See FIG. 10). In the non-actuated mode, the followers 82 of one link may be spaced apart from the closed end of the slots 80 of the adjacent link (See FIG. 9). As the steerable instrument 22 is actuated, the followers 82 follows the curve of the slots 80 until the end of the followers 82 contact the closed end of the slots 80. In the embodiment shown, the shaft 60 includes two slots 80 at its distal end 61. The followers 82 and slots 80 are configured such that longitudinally they are locked to one another. In other words, the followers 82 and the slots 80, when constrained inside the deformable conduit 24, provide for the links 74 being unable to be become disengaged from one another.

Figure 12:
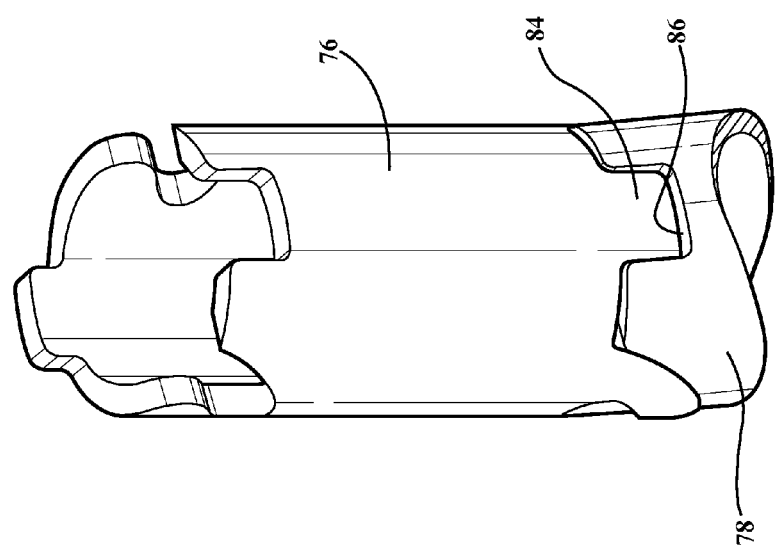
FIG. 12 is a perspective view of a first and second link of the plurality of interlocking links of FIGS. 9 and 10.

Referring to FIG. 12, the first link 76 may also comprise at least one protrusion 84 and the second link 78 may comprise at least one groove 86, with the protrusions 84 sized to be movably disposed within the grooves 86. Alternatively, the second link 78 may comprise the at least one protrusion 84 and the first link 76 comprise the at least one groove 86. Referring to FIG. 11, in the embodiment shown, the first and second links 76, 78 include both the two protrusions 84 and the two grooves 86 alternating on opposing ends. The interaction of the protrusions 84 and the corresponding grooves 86 provides additional torsional and lateral strength to the deflectable portion 48. The protrusions 84 of the deflectable portion 48 that faces in the direction of curvature may be spaced from an end surface forming the corresponding grooves 86 of the steerable instrument 22 when not actuated, and may directly contact the end surfaces forming the grooves 86 upon actuation. In one specific embodiment, the protrusions 84 and the grooves 86 may be configured in an interlocking shape, such as a trapezoid where the protrusions 84 are wider at the top of the protrusions and the grooves 86 is correspondingly wider at the bottom, which would add additional strength and stability to the plurality of links 74.

Referring to FIGS. 9 and 10, in certain embodiments, the intersection of the first link 76 and the second link 78 defines a gap 104 there between. The first link 76 and/or the second link 78 may comprise an angled portion 90 that defines a fulcrum 92 of rotation between the first link 76 and the second link 78. The angled portion 90 is arranged at an acute angle relative to end surface 94. By configuring the fulcrum 92 to be substantially coaxial with the curved surfaces of the slot 80 and follower 82, the plurality of links 74 maintain multiple points of contact with one another during actuation of the steerable instrument 22, which allows the plurality of links 74 to bear a substantial axial load via end surfaces 94 while the steerable instrument 22 is axially advanced through tissue, while also allowing the deflectable portion 48 of the steerable instrument 22 to exert a substantial lateral force on the deformable conduit 24 when the steerable instrument 22 is actuated. This allows the system and method to operate in harder tissue, such as non-osteoporotic cancellous bone without experiencing permanent deformation or failure. The length and angle of the angled portion 90 may be controlled to adjust the position of the fulcrum 92. The angled portion 90 may be angled at 10, 20, 30, 40, 50, 60, 70, or 80 degrees or more relative to the distal end surface 94 of the corresponding link.

Referring to FIGS. 14 and 15, an alternative deflectable portion 48a is shown that may be capable of deforming in multiple directions with the movable segment comprising a plurality of multi-directional links 94. In such an embodiment, each of the plurality of multi-directional links 94 typically comprises at least two actuation holes 96. The control element may comprise wires or cables disposed within each of these actuation holes 96, allowing the deflectable portion 48a to be articulated in multiple directions. By tensioning the control element that passes through a first actuation hole 96a to a greater degree than the control element that passes through a second actuation hole 96b, the deflectable portion 48a assumes a curved configuration in a particular direction. The multi-directional links 94 may further comprise the slots, followers, protrusions, and/or grooves described above. Alternatively, the multi-directional links may comprise a multi-directional fulcrum 98. The multi-directional fulcrum 98 may be rounded, such that the adjacent links may freely rotate in any direction as the deflectable portion 48a is actuated. Alternatively, the deflectable portion 48 may be uni-directional.

Alternatively, a plurality of movable segments may comprise a plurality of hinge joints joined by a spine (not shown). The plurality of hinge joints assists in the reversible deflection of the deflectable portion of the steerable instrument. A hinged side of the deflectable portion shortens under compression, while the spine side of the deflectable portion retains its axial length, causing the deflectable portion to assume a relatively curved or deflected configuration as the control element is activated. The plurality of movable segments may be manufactured by laser cutting, electrical discharge machining, water jet cutting, or other suitable manufacturing method using a single metal tube using a pre-defined pattern, such that the tube is pre-assembled. The steerable instrument may comprise Nitinol, stainless steel, or other suitable metal alloy.

In another embodiment, the steerable instrument 22 does not allow a material to pass there through, and can be configured to utilize larger and stronger components, which will result in a more robust tool that can easily displace cancellous bone. In the embodiment shown, the steerable instrument 22 comprises a control element 54 disposed in the lumen defined in part by shaft 60 and in part by the plurality of links 74, or movable segments. In one embodiment, the cross-sectional area of the lumen may be completely filled by the presence of the control element 54. Alternatively, at least 25%, 40%, 55%, 65%, 75%, 85%, or 95% of the cross-sectional area of the lumen of the steerable instrument 22 may be occupied by the control element 54. In the embodiment shown, the control element 54 substantially fills the lumen of the steerable instrument 22. Depending on the proportion of the lumen occupied by the control element 54, the lumen may function to allow the passage of the implant therethrough. Furthermore, the strength of the steerable instrument 22 may depend on the proportion of the lumen occupied by the control element 54.

Figure 16:
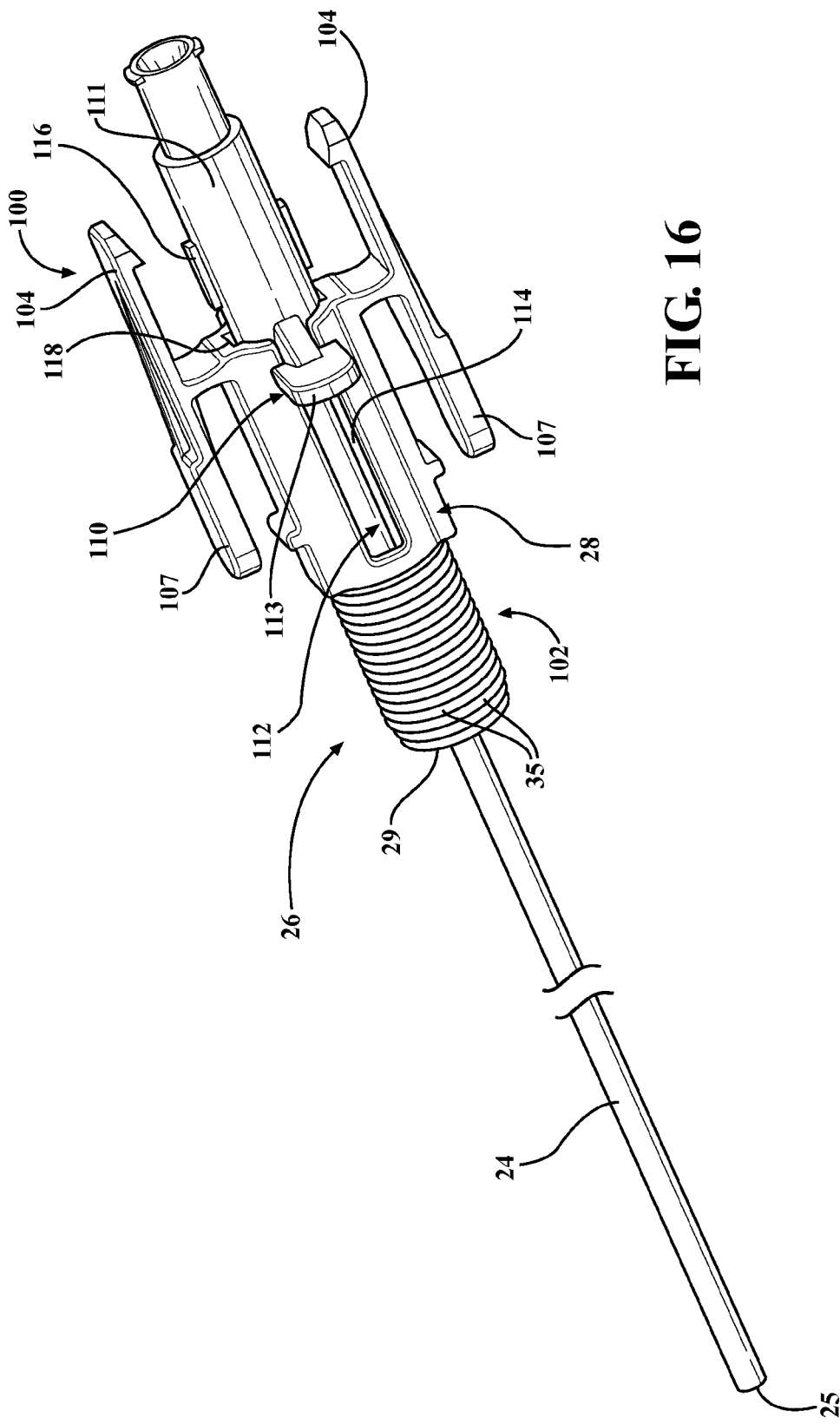
FIG. 16 is a perspective view of the deformable conduit assembly in accordance with one embodiment.
Figure 17:
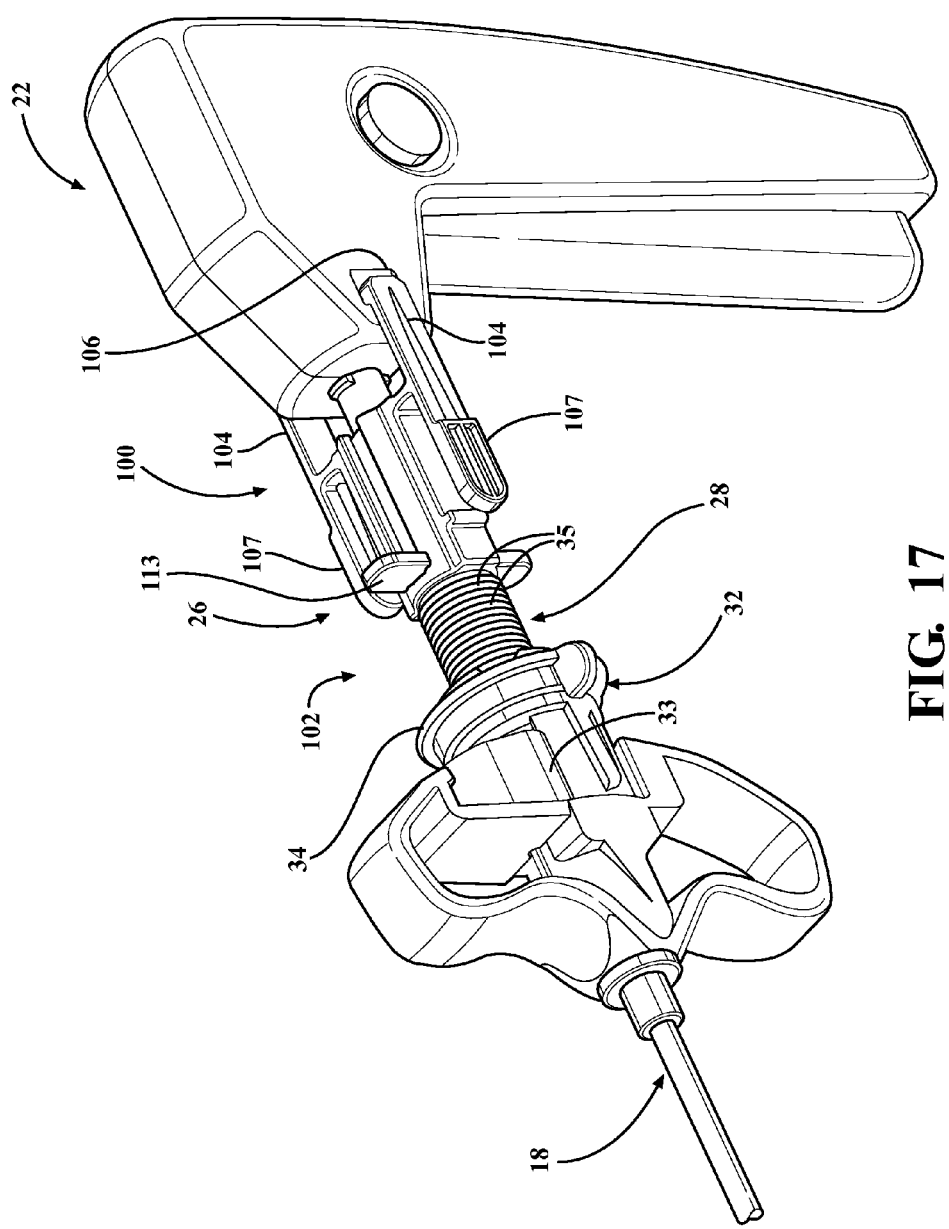
FIG. 17 is a perspective view of the steerable instrument connected to the hub of the deformable conduit assembly, which is connected to the cannula adapter of the access cannula.
Figure 18:
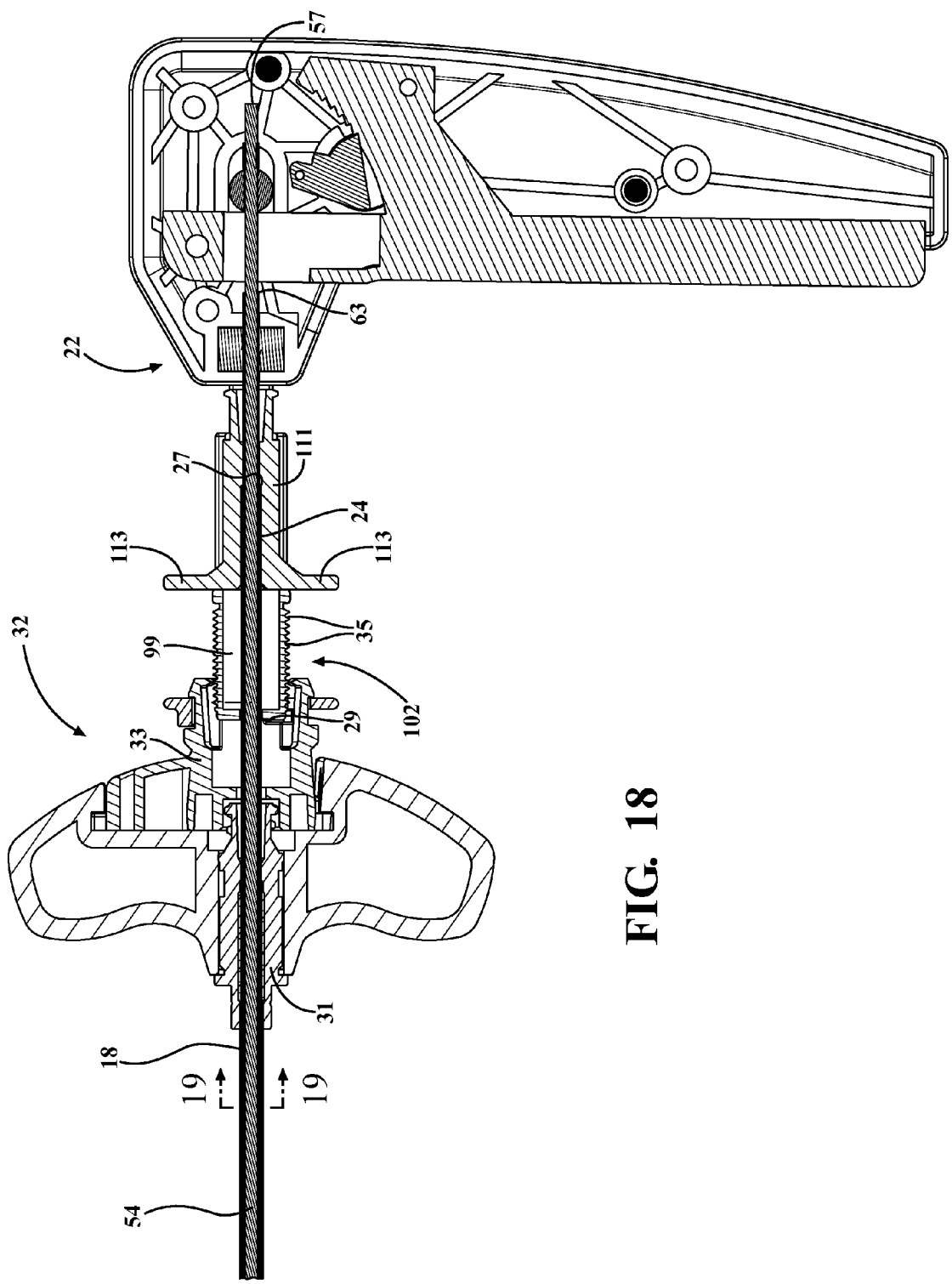
FIG. 18 is a cross-sectional view of FIG. 17.

Referring to FIGS. 16-18, the deformable conduit 24 defines a lumen dimensioned to allow the steerable instrument 22 to be slid through the deformable conduit 24. Referring to FIG. 1, the deformable conduit 24 is configured to retain the shape of the steerable instrument 22 when the steerable instrument 22 assumes the curved configuration and hence, the distal end 25 of the deformable conduit 24 is positioned at the desired location in the tissue.

The deformable conduit 24 is sized for insertion within the lumen of the access cannula 18 and includes a proximal end 27 and the distal end 25. The deformable conduit 24 is dimensioned to have a sufficient length to extend through and be operable beyond the distal end 21 of the access cannula 18. The deformable conduit 24 may be employed to deliver hardenable material to the target site. Thus, the deformable conduit 24 has an outer diameter that is smaller than a diameter of the lumen of the access cannula 18; however, the outer diameter of deformable conduit 24 preferably will not be so small as to allow hardenable material to readily travel around the outside of the deformable conduit 24 and back into the access cannula 18.

In certain embodiments, an inner lumen diameter of the deformable conduit 24 may be preferably optimized to allow a minimal exterior delivery pressure profile while maximizing the amount of hardenable material that can be delivered, such as bone cement. In one embodiment, the percentage of the lumen diameter with respect to the outside diameter of the deformable conduit 24 is at least about 60%, 65%, 70%, 75%, 80%, 85%, 95% or more.

The deformable conduit 24 may include depth markings (not shown) along a proximal section that facilitates desired locating of the distal end 25 of the deformable conduit 24 relative to the distal end 21 of the access cannula 18 during use. The deformable conduit 24 or the steerable instrument 22 may also include indicia (not shown) that show the direction of the curvature.

Referring to FIGS. 16 and 17, the hub 28 partially surrounds the deformable conduit 24 and is slidably coupled to the proximal end 27 of the deformable conduit 24. The hub 28 comprises a proximal hub connector 100, and a distal hub connector 102. The hub defines a central passage 99. The deformable conduit 24 is slidably disposed within the central passage 99 of the hub 28 such that the deformable conduit 24 can move in an axial direction relative to the hub 28. The hub 28 may comprise a polymeric material, such as ABS, nylon, polyether block amides, or other thermoplastic.

Referring to FIG. 17, the proximal hub connector 100 of the hub 28 is configured to connect to the steerable instrument 22, an expandable member, an implant delivery system, cavity creation tool, or other device. The proximal hub connector 100 may utilize a detent system to ensure that the hub 28 is axially fixed and rotationally fixed to the steerable instrument, expandable member, implant delivery system, etc. In such an embodiment, the proximal hub connector 100 may include one or more latches 104 with detent fingers (not numbered) extending proximally from the proximal hub connector 100 which are configured to releasably engage a notch 106, void, groove, or other connector of the steerable instrument, expandable member, or implant delivery system so that the hub 28 is axially and rotationally fixed to the steerable instrument, expandable member, etc. The distal end of the latch 104 may function as a lever 107, such that pressing the distal portion of the latch 104 towards the hub 28 results in the release of the detent system (the proximal end of the latch 104 is urged outward, thus releasing from the notch 106 of the corresponding component). It is also contemplated that the latch 104 and notch 106 could be replaced with other retention systems that are capable of fixing the hub axially and rotationally to the steerable instrument.

Referring to FIG. 18, the hub 28 is configured to connect to the access cannula 18 via the distal hub connector 102. The distal end 29 of hub 28 has an opening (not numbered)

through which the deformable conduit 24 slides during operation. In some embodiments, the distal hub connector 102 is configured to connect to the cannula adapter 32. The distal hub connector 102 includes the grooved section of hub 28 previously described. The distal hub connector 102 interacts with the cannula adapter 32 to form an axial locking mechanism. In one specific embodiment previously described, the grooved section of the distal hub connector 102 interacts with the lock ring 34 to lock the hub 28 and cantilever arms 42 of body 33 axially in place with respect to the access cannula 18, while allowing the hub 28, and the deformable conduit 24, to rotate relative to the access cannula 18. As described above, the grooved section of the distal hub connector 102 may comprise one or more spaced grooves 35 spaced to correspond to a specific predetermined depth of the deformable conduit 24 relative to access cannula 18 depending on which spaced groove 35 is engaged by the cannula adapter 32.

In another embodiment (not shown), the hub 28 may interact with the access cannula 18 in a manner that is not rigidly fixed. In such an alternative, the hub 28 employs axial force resulting from the flexure of a component or friction to resist relative movement of the access cannula 18 relative to the hub 28. This axial force may be provided from frictional forces arising from moving parts, or from interaction of one component with an elastomeric member, such as o-ring.

Referring again to FIG. 16, the deformable conduit assembly 26 may comprise an axial controller 110 configured to urge the deformable conduit 24 in the axial direction relative to the hub 28, within the distal end opening of the hub 28 and the access cannula 18, without moving the access cannula 18 or the hub 28 in the axial direction. The axial controller 110 comprises a conduit control surface 114 operatively connected to the deformable conduit 24. In such an embodiment, the hub 28 may comprise one or more guiding slots 112 that allow the conduit control surface 114 to be disposed there through. The conduit control surface 114 may be engaged to urge the deformable conduit 24 in a proximal or a distal direction relative to the hub 28. This may allow the clinician to expose the expandable structure 128 without disturbing the expandable member 126. The function may also be useful for urging the expandable structure 128 back into the deformable conduit 24 prior to withdrawal of the expandable structure 128 after use.

In the embodiment shown in FIG. 18, the axial controller 110 includes a control body 111 fixed to the proximal end 27 of the deformable conduit 24. The control body 111 has a diameter smaller than the passage 99 of the hub 28 such that the control body 111 may be slidably disposed in the hub 28. The control body 111 may comprise a tube concentrically fixed on the outer circumference of the deformable conduit 24. The control body 111 may be coaxially positioned within the passage 99 of the hub 28. The axial controller 110 comprises one or more arms 113 extending from the control body 111. The arms 113 may be dimensioned and oriented to protrude though the guiding slots 112. Each of slots 112 has a closed end that acts as a stop for the arms 113 to limit the amount of distal movement of the deformable conduit 24. The arms 113 present the conduit control surfaces 114. Alternative conduit control surfaces 114 are also contemplated, such as threaded surfaces, a helical slot and follower, or rack and pinion device. In one example, a clinician may urge the conduit control surface 114 axially to urge the deformable conduit 24 axially, such that the axial position of the deformable conduit 24 changes relative to the access cannula 18 and relative to the hub 28. In another example, indicia (visible, tactile, or audible) may be provided with the deformable conduit 24 or expandable structure 128 to allow the clinician to set a precise amount of desired exposure of the expandable structure 128, thus allowing the deformable conduit 24 to affect the proportion of the expandable structure 128 that contacts tissue.

The axial controller 110 may also function to guide the deformable conduit 24 such that the deformable conduit 24 does not rotate relative to the hub 28 of the deformable conduit assembly 26. In one specific embodiment, this guiding function may be accomplished by positioning the conduit control surfaces 114 within the one or more guiding slots 112 of the hub 28 such that the conduit control surfaces 114 are constrained rotationally relative to the hub 28, and therefore prevent the deformable conduit 24 from rotating relative to the hub 28. The arms 113 may simultaneously prevent the hub 28 from rotating relative to the deformable conduit 24. Thus, the rotational arrangement of the hub 28 and the deformable conduit 24 may be rotationally fixed to one another.

Alternatively, or in addition to such an embodiment, the control body 111 may comprise an alignment feature 116 which ensures that the control body 111 does not rotate in the passage 99 relative to the hub 28. The alignment feature 116 may comprise a protrusion sized to slide within a channel 118 disposed in the hub 28. The protrusion 116 and the channel 118 may be complementarily dimensioned such that the protrusion 116 may slide longitudinally within the channel 118 as the deformable conduit 24 moves relative to the hub 28.

As shown in FIG. 16, the control body 111 may comprise a proximal end defining a proximal abutting surface. The proximal abutting surface may abut a distal abutting surface of the handle 56 of the steerable instrument 22 when the steerable instrument is rotationally and axially locked to the hub 28, thereby constraining axial movement of the deformable conduit 24 so that the deformable conduit 24 does not move axially relative to the steering instrument 22 during insertion of the steerable assembly 20 in the access cannula 18 and the vertebra 10.

In other embodiments, the hub 28 is not employed and the deformable conduit 24 is deployable in the access cannula 18. In these embodiments, a handle may be fixed to the deformable conduit 24. The deformable conduit 24 may be moved relative to the access cannula 18 to control the placement of the distal end 25 of the deformable conduit 24.

Referring to FIGS. 19 and 20, in certain embodiments, the deformable conduit 24 may be a multi-layer, internally-reinforced, tube. This allows the deformable conduit 24 to potentially possess a combination of attributes; including high hoop strength to resist internal pressure, high axial strength for pushability, and a low lateral stiffness to allow the deformable conduit 24 to maintain the deformed position in softer tissues. In the embodiment shown, the deformable conduit 24 comprises a reinforcement 120, a liner 122, and/or a sheath 124. However, it is also contemplated that the multi-layer tube may include 2, 4, 5, 6, or more layers. The reinforcement 120 typically comprises a braid, a coil, weave, or one or more longitudinal strands of reinforcing material. The reinforcing material may possess a circular, flattened rectangular, or oval cross-section, in order to optimize strength and stiffness properties while minimizing radial thickness. The reinforcing material typically comprises metal, fabric, plastic, fiberglass or alternative materials that have minimal elasticity upon deformation. In one specific embodiment, the reinforcement 120 comprises a braid comprising stainless steel.

The liner 122 may comprise a lubricious polymer. The lubricious polymer is a material that allows components such as the steerable instrument 22 to easily slide adjacent to the liner 122. The liner 122 is typically inert and biologically compatible. In exemplary embodiments, the inner liner 122 comprises a fluoropolymer, PEBA, nylon, or combinations thereof. The inner liner 122 may be coated with a lubricant or coating to enhance lubricity, abrasion resistance, or another desired property.

The sheath 124 may comprise a polymer that is capable of resisting abrasion while contacting hard tissue or the access cannula 18 and is sufficiently strong to traverse hard tissue, such as bone. For example, the sheath 124 may comprise a thermoplastic elastomer, such as a polyether block amides or nylon.

The reinforcement 120, the liner 122, and the sheath 124 may be distinct layers. Referring to FIG. 19, the reinforcement 120, the liner 122, and the sheath 124, may be concentrically arranged, with each element forming a distinct layer of the deformable conduit 24. Alternatively, the reinforcement 120 may be at least partially embedded in the liner 122, the sheath 124, or both the liner 122 and the sheath 124. Alternatively still, the reinforcement 120 may be completely embedded in single polymeric tube, with no other layers being present.

Referring to FIG. 20, the density of the reinforcement 120 may vary along the longitudinal dimension of the deformable conduit 24. For example, a distal portion of the deformable conduit 24 may include less of the reinforcement material per centimeter than a proximal portion to allow for improved flexibility of the distal portion of the deformable conduit 24 or improved pushability of the proximal portion of deformable conduit 24. Alternatively, the amount of the reinforcement material in the deformable conduit 24 at the distal portion may be equal to, or less than the density of the reinforcement material at the proximal portion. It is also contemplated that the reinforcement 120 may not extend the entire length of the deformable conduit 24; rather, the reinforcement 120 may be provided in less than 90, 75, 50, or 25% of the length of the deformable conduit 24.

Figure 21:
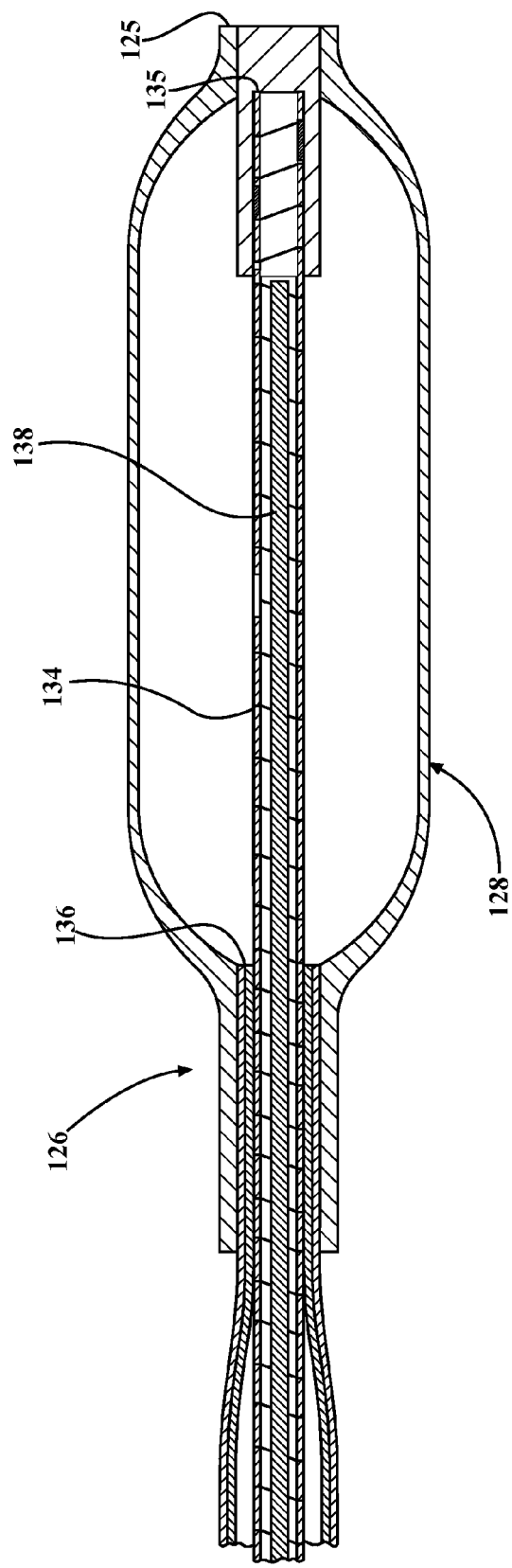
FIG. 21 is a cross-sectional view of an expandable member in accordance with one embodiment.
Figure 22:
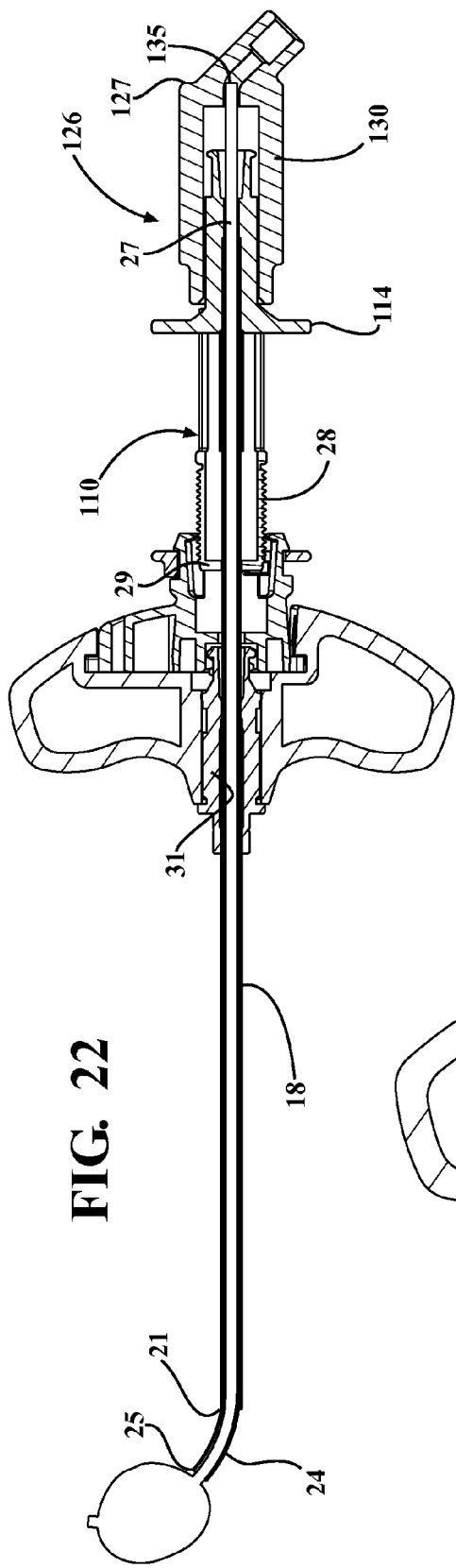
FIG. 22 is a cross-sectional view of an expandable member connected to the deformable conduit assembly.
Figure 23:
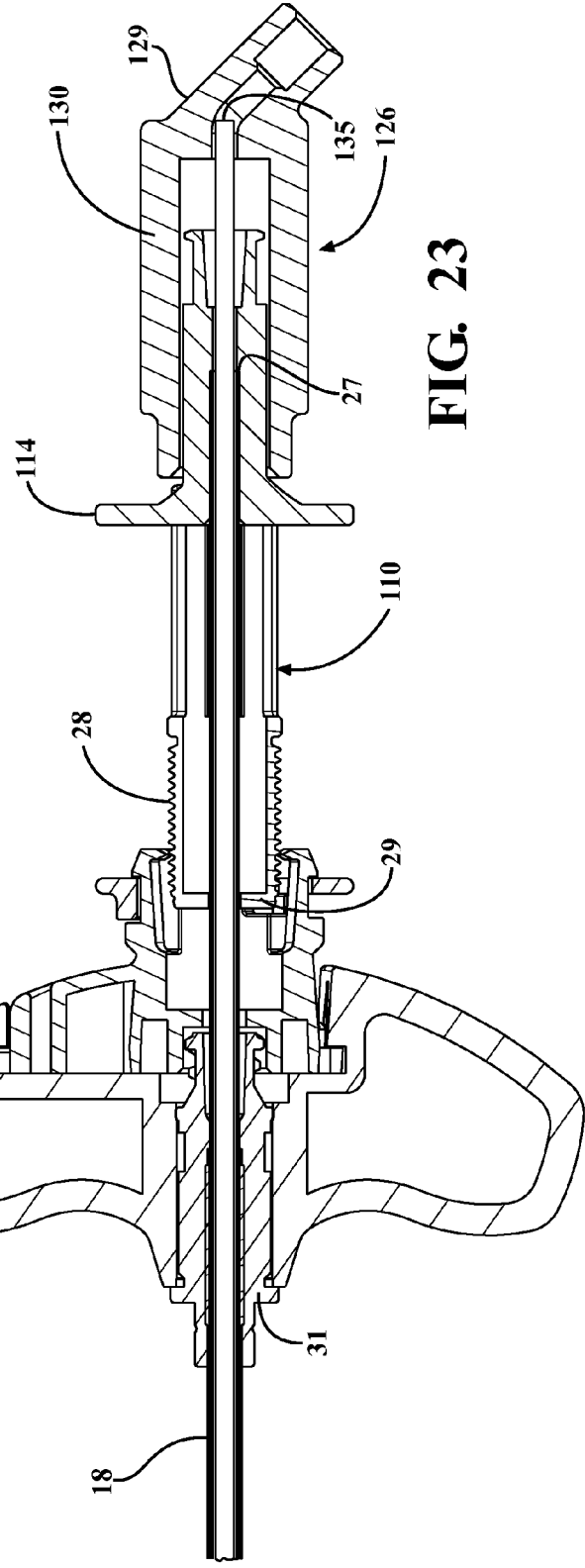
FIG. 23 is a close-up cross-sectional view of FIG. 22.

Referring to FIGS. 21-23, in certain embodiments, the system further comprises an expandable member 126. The expandable member 126 may comprise an expandable structure 128, such as a balloon, stent, flexible bands (such as metal bands) or other device capable of increasing in size in the radial direction. In certain embodiments, the expandable structure 128 is capable of expanding to a diameter to a size larger than the diameter of the deformable conduit 24. The expandable member 126 is typically biocompatible and dimensioned and configured to be inserted through the deformable conduit 24 in the deformed position. The expandable member 126 may further comprise one or more components appropriate for forming a cavity or void within tissue. Alternative to the expandable member, the system may employ an alternative cavity creation tool that does not expand to create the cavity.

In some constructions, the expandable member 126 may include one or more inflatable members (e.g., a single balloon, multiple balloons, a single balloon with two or more discernable inflation zones) constructed to transition between a contracted state in which the inflatable member may be passed through the lumen of the deformable conduit 24 or the access cannula 18, and an expanded state in which the inflatable member expands and displaces cancellous bone 16 or other tissue.

Referring to FIG. 21, in the illustrated embodiment, the expandable member 126 typically includes an inner catheter tube 134 having a distal end 135. The inner catheter tube 134 may comprise vinyl, nylon, polyethylenes, ionomer, polyurethane, and polyethylene tetra phthalate (PET). The inner catheter tube 134 may further comprise one or more rigid materials to impart greater stiffness and thereby aid in its manipulation, such as stainless steel, nickel-titanium alloys (Nitinol™ material), and other metal alloys. The inner catheter tube 134 may include multiple holes to allow inflation fluid to pass from the proximal end of the expandable member 126, through the inner catheter tube 134, in order to inflate the expandable structure 128.

The expandable member 126 may further comprise an outer catheter tube 136. The outer catheter tube 136 may comprise multiple layers, or multiple concentric tubes. The inner layer of the outer catheter tube 136 may comprise a relatively stiff polymer for pressure resistance, and the outer layer of the outer catheter tube 136 may comprise a relatively soft polymer that allows for adhesion between the outer layer and the expandable structure 128. The distal end of the outer catheter tube 136 may abut the proximal end of the expandable structure 128. The outer catheter tube 136 may be partially disposed within the expandable structure 128, with the outer layer of the catheter tube 136 bonded to the proximal end of the expandable structure 128.

In some embodiments, at least a portion of the inner catheter tube 134 may be configured with relief features to allow the inner catheter tube 134 to bend freely to allow for advancement through the deformable conduit 24 while minimizing undesired movement of the deformable conduit 24. The relief features may comprise grooves, thinned areas, or a helical spiral cut through the inner catheter tube 134. In the embodiment shown, the inner catheter tube 134 comprises a helical spiral cut. The helical spiral cut may improve the pushability of the expandable member 126 by acting as a spring compressed to solid height.

For embodiments where the inner catheter tube 134 is spirally cut, the pitch of the spiral cut may vary along the longitudinal dimension of the inner catheter tube 134. For example, the distal portion of the inner catheter tube 134 may have a greater concentration of cuts per centimeter than the proximal portion to allow for improved flexibility of the distal portion of the inner catheter tube 134 relative to the proximal portion. Alternatively, the proximal portion of the inner catheter tube 134 may have a lesser concentration of cuts per centimeter to allow for improved stiffness and pushability of the proximal portion of the expandable member 126. The spiral cut may be pitched at a ratio ranging from 0.1 to 10 rotations per centimeter of the inner catheter tube 134 depending on the desired stiffness of the inner catheter tube 134. Alternatively, the spiral cut may be pitched at a ratio ranging from 0.5 to 8, or 1 to 3, rotations per centimeter of the inner catheter tube 134. It is also contemplated that the outer catheter tube 136 may comprise one or more relief structures in a manner similar to the inner catheter tube 134 described above.

In certain embodiments, the expandable member 126 may comprise a stylet 138. The stylet 138 can be flexible or rigid, and may comprise a plastic, or metal material. The stylet 138 may be dimensioned and configured to slide in a lumen of the inner catheter tube 134, or in the gap between outer catheter tube 136 and inner catheter tube 134.

The stylet 138 may include a threaded coupling to secure the stylet 138 to the expandable structure 128 to prevent movement of the stylet 138 during deployment of the expandable structure 128. The presence of the stylet 138 provides axial strength as the expandable structure 128 is urged through the access cannula 18 or the deformable conduit 24. Once the expandable structure 128 is free of the deformable conduit 24 (or the access cannula 18) and is disposed within tissue, the stylet 138 can be withdrawn. The lumen of the inner catheter tube 134 (or the gap between outer catheter tube 136 and inner catheter tube 134) can serve as a pathway for inflating the expandable member 126, introducing rinsing liquid, to aspirate debris from the tissue, or to introduce hardenable material, such as bone cement. The inner catheter tube 134 may contain at least one opening in fluid communication with the inner volume of the expandable structure 128. Alternatively, the inner catheter tube 134 or the gap between inner catheter tube 134 and outer catheter tube 136 may contain at least one opening in fluid communication with the tissue being treated.

In one specific embodiment, the inner catheter tube 134 may be disjoined from the outer catheter tube 136 and slidably disposed on the stylet 138, such that during expansion of the expandable structure 128, the inner catheter tube 134 is urged distally from outer catheter tube 136. The inner catheter tube 134 may be configured to exert no axial force on expandable structure 128. Alternatively, the inner catheter tube 134 may be configured to exert an axial force on the expandable structure 128 to affect the expanded shape.

In certain embodiments, an object or device may be inserted into inner catheter tube 134 to allow the clinician to apply force to expandable member 128. This device may comprise the stylet 138 configured in a pre-formed shape to allow directional control of the expandable member 126. Alternatively, a device similar to the steering instrument 22, but having different dimensions, may be inserted into inner catheter tube 134 for further control of the expandable member 126.

As an alternative to the inner catheter tube 134, a solid member may be utilized (not shown). In such an embodiment, the gap between the solid member and the outer catheter tube 136 may allow fluid to enter and expand the expandable structure. The solid member may comprise one or more of medical alloys and polymeric materials described above. The solid member may comprise one of more of the relief features described above with respect to the inner catheter tube.

The expandable structure 128 may comprise a plurality of shapes, such as an hour-glass, spherical, elliptical, rectangular, pyramidal, egg-shaped, or kidney-shaped. In certain embodiments, the size and shape of the expandable structure 128 may be restrained with one or more additional components, such as internal and/or external restraints. In preferred embodiments the expandable structure 128 will be structurally robust, able to withstand (e.g., not burst) expected inflation pressures when in contact with tissue. The expandable member 126 may further comprise one or more additional components connected or operable through the proximal region for actuating the corresponding expandable member 126, such as an inflator.

In another embodiment, the expandable member 126 may include a plurality of expandable structures 128. The number of expandable structures 128 utilized in the procedure may be controlled by utilizing separate actuation passages (e.g. lumens) or members within in the expandable member 126, or by using the deformable conduit 24 to expose only the desired number of expandable structures to the tissue. Indicia (visible, tactile, or audible) may be provided to indicate the number of expandable structures 128.

Referring to FIGS. 22 and 23, the expandable member 126 may comprise a housing 130, having one or more detent features, such as notches, such that the housing 130 of the expandable member 126 can be axially fixed relative to the access cannula 18 and so that the position of the expandable structure 128 does not move relative to the access cannula 18. This connection be accomplished using the latches 104 similar to the connection of the steering instrument 22 to the hub 28. This serves to prevent inadvertent axial movement of the expandable member 126 that may occur during retraction of the deformable conduit 24 or actuation of the expandable member 126. In one embodiment, the housing 130 of the expandable member 126 is configured to connect to the hub 28 of the deformable conduit assembly 26. The hub 28 may fixedly engage the housing 130 or some other portion of the expandable member 126, to axially fix the position of the expandable structure 128 relative to the position of the access cannula 18, such that the deformable conduit 24 may move axially relative to the access cannula 18 without moving the expandable member 126, including not moving the expandable structure 128. The housing 130 may have features to facilitate gripping and maneuvering of the expandable member 126. Finally, the housing 130 may include features for attachment to another instrument, such as an inflator.

In one preferred embodiment, the expandable member 126 is dimensioned to extend through the deformable conduit 24 such that the distal end 127 of the expandable member 126, upon insertion into the deformable conduit 24, does not protrude beyond the distal end 25 of the deformable conduit 24 when the deformable conduit 24 is fully deployed. In this configuration, the expandable structure 128 stays within the lumen of the deformable conduit 24 until the deformable conduit 24 is retracted. This facilitates easier and more accurate introduction of the expandable member 126 into the desired location by not requiring the expandable member 126 to displace tissue during deployment, and may protect the expandable structure 128 from external damage during introductory movement into tissue.

The access cannula 18, steerable instrument 22, deformable conduit 24, and/or the expandable member 126 may include one or more visual indicia (e.g., markings on the clinician-held end, radio-opaque indicia at or near the distal end), tactile indicia (e.g. change in axial force felt by the clinician), or audible indicia (e.g. clicking sounds) that enable a clinician to determine the relative positions of those components to perform the methods described below.

Figure 24:
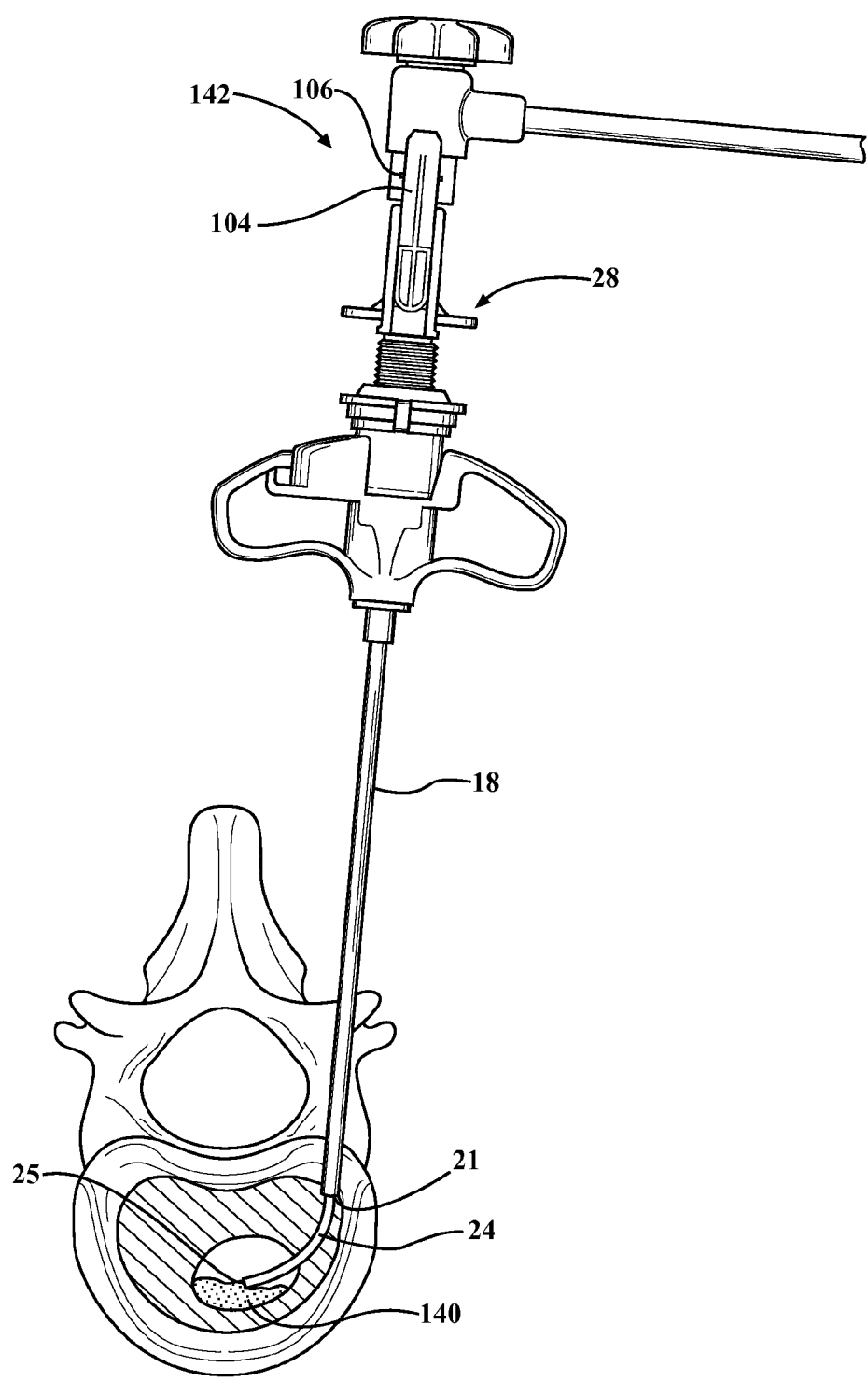
FIG. 24 is a top view of an implant delivery system connected to the deformable conduit assembly.

Referring to FIG. 24, the system may further comprise an implant 140 and an implant delivery system 142. The implant 140 may comprise a biocompatible material that is configured to remain adjacent to tissue permanently, semi-permanently, or temporarily. The implant 140 may comprise a hardenable material, bag, sheath, stent, and/or any combination thereof.

The phrase "hardenable material" is intended to refer to materials (e.g., composites, polymers, and the like) that have a fluid or flowable state or phase and a hardened, solid or cured state or phase. Hardenable materials may include, but are not limited to, injectable bone cements (such as polymethylmethacrylate (PMMA) bone curable material), which have a flowable state wherein they may be delivered (e.g., injected) by a cannula to a site and subsequently cure into hardened, cured material. Other materials such as calcium phosphates, bone in-growth materials, antibiotics, proteins, etc., may be used in place of, or to augment the hardenable material. Mixtures of different hardenable materials may also be used.

The implant delivery system 142 may assume various forms appropriate for delivering the desired implant 140 (e.g., for delivering the hardenable material or other implant type). In certain embodiments, the implant delivery system 142 may comprise a chamber filled with a volume of hardenable material and any suitable injection system or pumping mechanism to transmit the hardenable material out of the chamber and through the deformable conduit 24. Alternatively, the implant delivery system 142 may comprise a hand injection system where a clinician applies force by hand to a syringe. The force is then translated into pressure on the hardenable material which causes the hardenable material to flow out of the syringe. A motorized system may also be used to apply force. A nozzle may be connected to the implant delivery system 142. The nozzle may comprise a tube configured for coaxial insertion into the deformable conduit 24, thus allowing delivery of material through the deformable conduit 24 without contacting the inner walls of the deformable conduit 24.

The implant delivery system 142 may connect to the deformable conduit 24 such that the implant 140 may be delivered through the lumen of the deformable conduit 24 to the target site. The implant delivery system 142 may connect to the proximal end of the hub 28 such that the deformable conduit 24 can be gradually or immediately retracted during the step of placing the implant 140. This locking can be accomplished using the latches 104 of the hub 28 to engage one or more notches located on the implant delivery system, similar to the notches of the expandable member 126. Another embodiment may include an adapter configured to allow attachment of a cement cannula (e.g., a rigid tube configured to be filled with hardenable material) to the deformable conduit 24, thus allowing the clinician to urge material through the deformable conduit 24 by using an instrument to displace material from the cement cannula.

In yet another embodiment, the system may comprise an aspiration device. The aspiration device functions to extract unwanted tissue, marrow products (blood precursors and marrow fat) that get displaced during performance of the described method. The system may be configured for aspiration from a lumen or gap within or between parts (e.g. a lumen within the expandable member 126 or deformable conduit 24, from the gap between the expandable member 126 and the deformable conduit 24, or from the gap between the deformable conduit 24 and the access cannula 18). The aspiration device may comprise a suction port and a seal that allows passage of instruments while preventing escape of fluids (i.e. a hemostasis valve) that attaches to or is integral to the access cannula 18 or the deformable conduit 24. The hemostasis valve may also connect to a suction tube. The hemostasis valve may be connected to a vacuum pump or a vacuum-generating syringe, and may have a check valve a fluid/tissue collection chamber. If performing a bi-pedicular procedure, the aspiration device could be used to aspirate on the contra lateral side which could influence the implant 140 to come across the midline. The aspiration device may be integrated with the implant delivery system 142 or may be used independently of the implant delivery system 142. The aspiration device may be utilized in combination with the various devices and methods disclosed herein.

This disclosure also relates to a surgical method for manipulating tissue. The method may comprise providing the access cannula 18, the steerable assembly 20, and the implant 140. The steerable assembly 20 comprises the steerable instrument 22 and the deformable conduit 24 with the steerable instrument 22 removably disposed within the deformable conduit 24.

Referring again to FIG. 1, the target site for manipulation may be identified by a clinician. Identification of the target site may include locating a pre-determined location within tissue for surgical intervention. In one embodiment, identifying the target site may comprise locating a central location in the cancellous bone 16 of the vertebra 10 that will support height-restoration and/or structural augmentation that preferably is at least generally symmetrical with respect to the vertebra 10. Several distinct methods are described herein. Although they are described individually, it is to be appreciated that the steps may be interchangeable and may be substituted with one or more alternative steps.

The following methods may be accomplished under either a local anesthetic or short-duration general anesthetic. The procedure is typically performed using intraoperative imaging such as fluoroscopy or CT. Once the area of the spine is anesthetized, an incision is made and a penetrating guide pin may be used to perforate the tissue and gain access to the target site. An expander may be slid over the guide pin to further retract tissue. The clinician slides the access cannula 18 over the expander and guide pin until the end surface of the access cannula 18 penetrates the vertebra 10. The clinician then removes the guide pin and expander and inserts the drill to create a channel in the cortical bone 14. The clinician can now remove the drill leaving only the access cannula 18. In alternative embodiments, the guide pin and/or an expander are not used, but instead, the access cannula 18 is placed through the tissue with an access stylet coaxially locked to the access cannula. The access stylet has a sharp distal end to core into the cortical bone of the vertebra 10. The access cannula 18 may have a similarly sharp distal end 21 to penetrate the vertebra 10 with the access stylet. Once the access cannula 18 is in place in the cancellous bone 16, the access stylet is removed. Once the channel through the pedicle 12 and into the vertebra 10 is created, various methods may be used to stabilize the subject vertebra 10.

Referring to FIG. 1, the method may further comprise directing the steerable assembly 20 through the access cannula 18 such that at least a portion of the steerable assembly 20 protrudes from the distal end 21 of the access cannula 18 into tissue at the target site. More specifically, the method may include positioning the steerable instrument 22 in the deformable conduit 24 until the latches 106 lock into the notches 106 in steerable instrument 22 and then sliding this steerable assembly 20 through the access cannula 18 to the target site. The fluoroscope imaging is continuously observed during insertion to verify placement of the deformable conduit 24 into the target tissue. If the steerable instrument 22 includes depth markings, the appropriate depth marking of the steerable instrument 22 will be aligned with the corresponding line on the access cannula 18 as additional confirmation that the distal end of the steerable instrument 22 is extended to the target site in the tissue to be manipulated.

As the steerable instrument 22 is advanced out of the distal end 21 of the access cannula 18, the steerable instrument 22 may be simultaneously actuated while the deflectable portion 48 of the steerable instrument 22 is disposed within the deformable conduit 24 to move the distal end 23 of the steerable instrument 22 and the distal end 25 of the deformable conduit 24 away from the longitudinal axis A of the access cannula 18 such that the deformable conduit 24 occupies the deformed position. The step of actuating the steerable instrument 22 comprises deflecting the deflectable portion 48 of the steerable instrument 22 to the curved configuration. As the steerable instrument 22 is actuated to cause the deflectable portion 48 to curve, the distal end 25 of the deformable conduit 24 moves in the same direction, resulting in the formation of a channel, void, or cavity in the tissue. The clinician can influence the size and shape of the channel based on the degree of actuation of the steerable instrument 22 and whether the steerable instrument 22 is rotated during actuation.

The deformed position is defined as a position of the deformable conduit 24 assumed after the steerable instrument 22 urges the distal end 25 of the deformable conduit 24 away from the distal end of the access cannula 18. Accordingly, the deformable conduit 24 can assume a variety of deformed positions, each having a different angle of curvature and radius based on the position of the distal end 25 of the deformable conduit 24 relative to the longitudinal axis A of the access cannula 18. In this manner, a clinician may determine a desirable curvature to reach the target site and actuate the steerable instrument 22 to a degree sufficient so that the deflectable portion 48 assumes the desired angle of curvature and radius, which in turn deforms the deformable conduit 24 to assume substantially the same angle of curvature. The clinician is able to observe the placement of the various components under intraoperative imaging due to inherent radiopacity of certain elements of the steerable assembly 20

The step of actuating the steerable instrument 22 comprises manually engaging the control surface 58. This manual engagement may comprise squeezing, rotating, or sliding the control surface 58 to actuate the control element 54 of the steerable instrument 22. The clinician may obtain feedback on the degree of actuation from indices previously described (visible, tactile, audible) and by direct visualization steerable assembly 20 in the tissue with intraoperative imaging. Actuation of the control element 54 (or control surface 58) may be performed at any time during the advancement of steerable assembly 20, including before, during, or after the distal end of the steerable assembly 20 has entered the tissue. There may be certain advantages to actuating before the steerable instrument 22 begins exiting distal end of the access cannula 18. This causes potential energy to be stored within the steerable instrument 22, which results in immediate lateral deflection of the deflectable portion 48 of steerable instrument 22 as the steerable instrument 22 is advanced distally from the access cannula 18. The clinician may employ feedback from the device (visible, tactile, or audible) to impart a desired amount of energy to the mechanism that will result in a desired amount of curvature upon advancement. If the steerable instrument 22 includes a locking mechanism as described before, the clinician may stop applying force to the control element 54 (or control surface 58) and allow the locking mechanism to retain and release the stored energy during advancement of the steerable assembly 20. This may allow the clinician to focus less attention on actuating the steerable instrument 22 and more on safely reaching the target location in the tissue.

The method may, upon reaching the target tissue, comprise locking the hub 28 of the deformable conduit assembly 26 at least axially in place with respect to the access cannula 18, which allows passage or withdrawal of instruments within the deformable conduit 24 without moving the deformable conduit 24. The locking mechanism may allow the deformable conduit 24 to rotate relative to the access cannula 18 to facilitate rotation of the steering instrument 22 or other instrument disposed within the deformable conduit 24. In one exemplary embodiment, the step of locking the hub 28 of the deformable conduit assembly 26 axially in place with respect to the access cannula 18 comprises rotating the lock ring 34 to lock the hub 28 of the deformable conduit assembly 26 in place.

Figure 25:
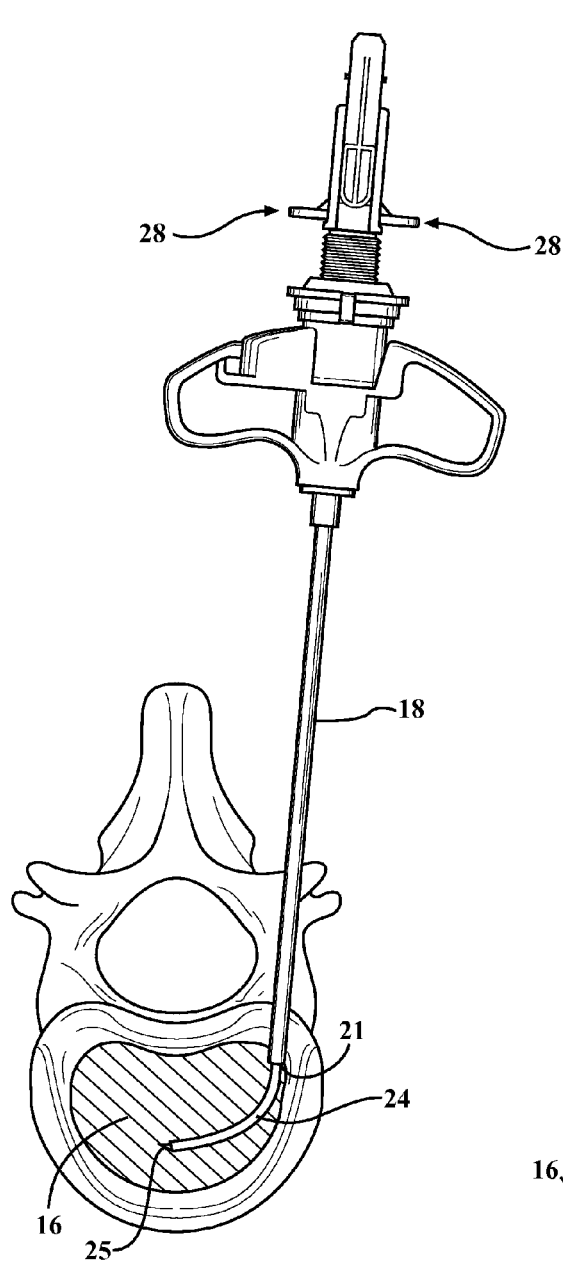
FIG. 25 is a top view of the deformable conduit assembly placed inside the access cannula, with the deformable conduit in the deformed position.

Referring to FIG. 25, the method may further comprise retracting and removing the steerable instrument 22 from the deformable conduit 24 after actuation of the steerable instrument 22. This includes retracting the steerable instrument 22 from the deformable conduit 24 when the control element 54 is operating in the slack tension mode without causing the deformable conduit 24 to deviate substantially from the deformed position. The steerable instrument 22 is generally retracted in an axial direction from within the deformable conduit 24 such that the deformable conduit 24 is no longer occluded by the steerable instrument 22 and can allow other components to be disposed within the lumen of the deformable conduit 24, such as the expandable structure 128 or the implant 140.

In certain embodiments, the method may comprise releasing the tension of the steerable instrument 22 before retracting the steerable instrument 22 from the deformable conduit 24 such that the distal end 23 of the steerable instrument 22 is adapted to readily conform to the deformed position of the deformable conduit 24 without causing the deformable conduit 24 to be substantially displaced from the deformed position. In one embodiment, the step of releasing may comprise operating in the slack tension mode of the steerable instrument 22. By releasing the tension of the steerable instrument 22 before retracting, the deformable conduit 24 is less likely to be deformed by the retraction of the steerable instrument 22. Reducing the amount of deformation ensures that the distal end 25 of the deformable conduit 24 remains adjacent to the target site, which allows precise placement of the implant 140 and/or the expandable structure 128.

Figure 26:
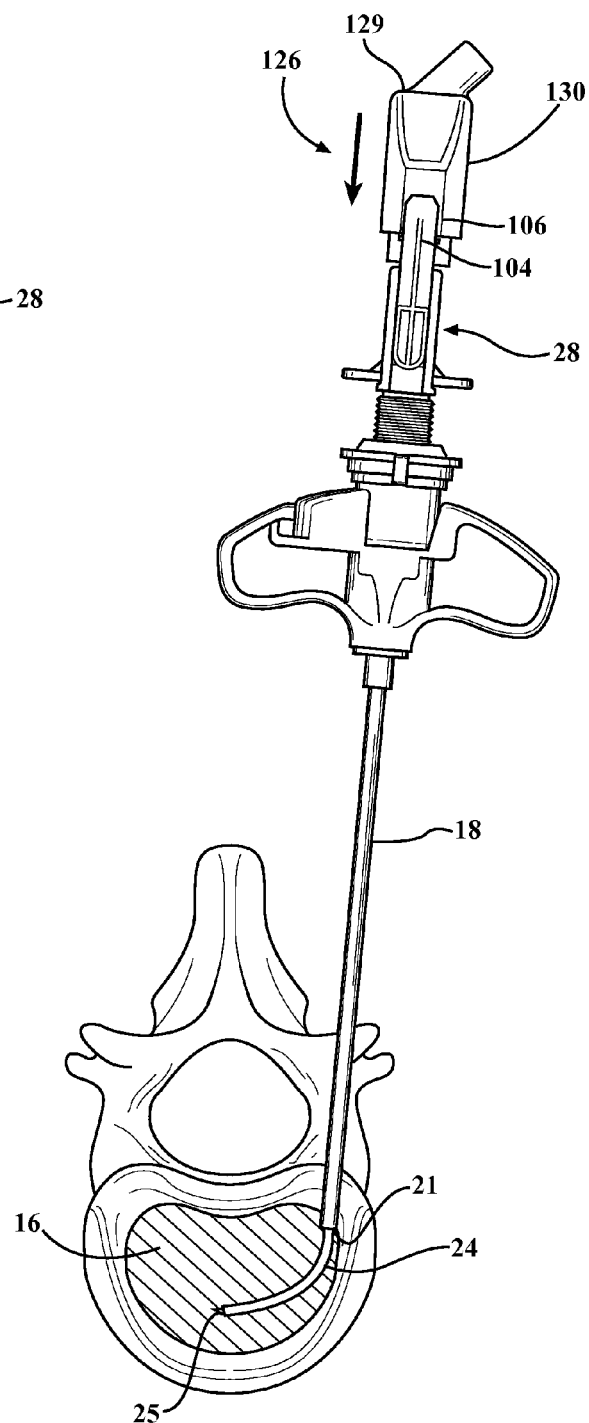
FIG. 26 is a top view of the deformable conduit assembly placed inside the access cannula, with the deformable conduit in the deformed position, and the expandable member inserted therein.
Figures 27, 28:
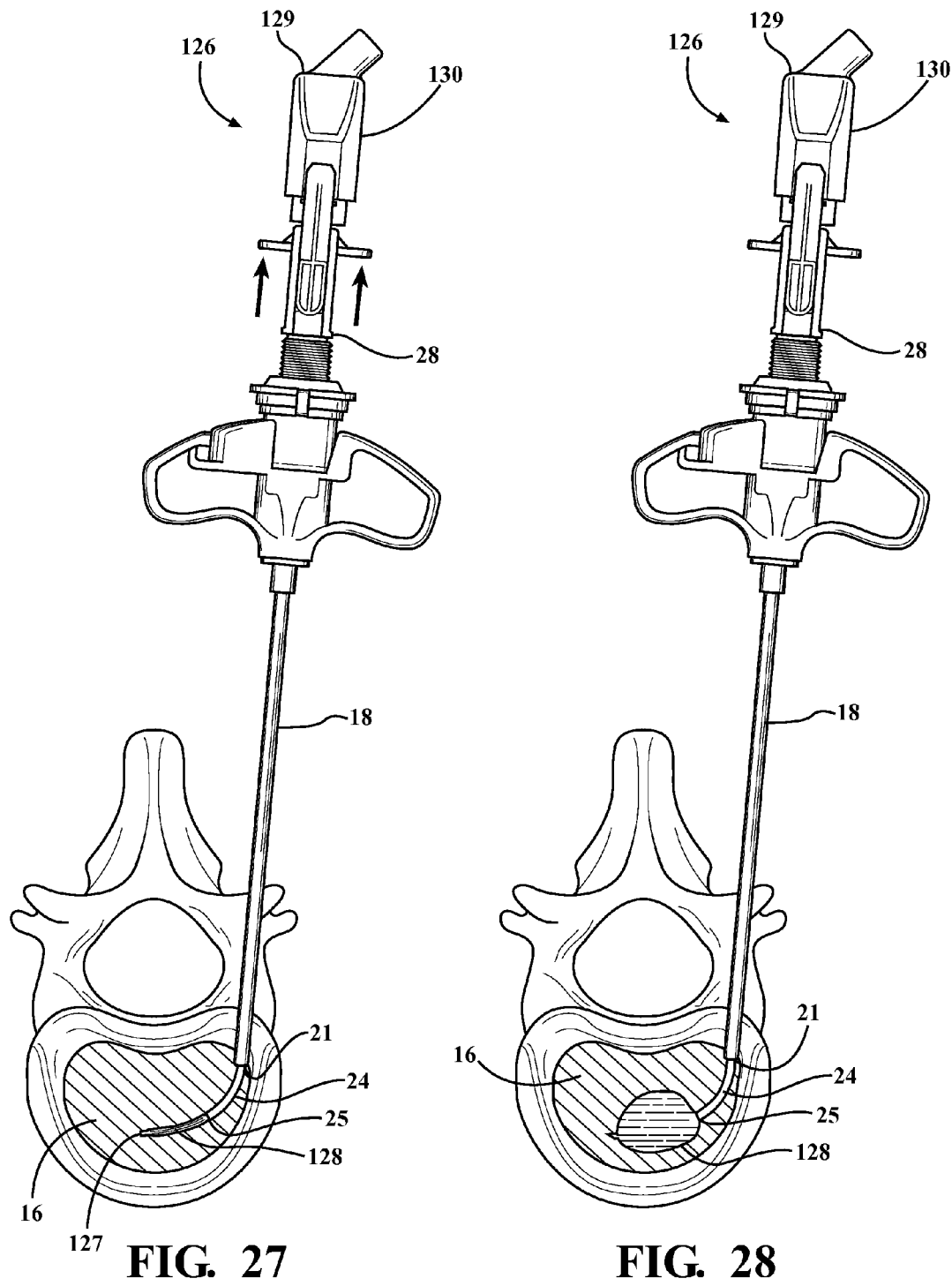
FIG. 27 is a top view of the deformable conduit assembly placed inside the access cannula, with the deformable conduit in the deformed position, and the expandable member inserted therein, with the deformable conduit retracted to uncover an expandable structure.
FIG. 28 is a top view of the deformable conduit assembly placed inside the access cannula, with the deformable conduit in the deformed position, and the expandable member inserted therein, with the deformable conduit retracted to uncover the expandable structure, and the expandable structure in an expanded condition.

Referring to FIGS. 26-28, in some embodiments the expandable member 126 is utilized. The method comprises inserting the expandable member 126 through the deformable conduit 24 (FIG. 26), retracting the deformable conduit 24 to expose the expandable structure 128 (FIG. 27), and expanding the expandable structure 128 to form a cavity in the tissue (FIG. 28). In such embodiments, the step of placing the implant 140 is further defined as placing the implant 140 at least partially within the cavity formed by the expandable structure 128. Once the cavity is formed, the expandable structure 128 may then be returned to its contracted (e.g., deflated) state, and retracted from the deformable conduit 24.

The clinician identifies the shape of the tissue to be displaced and the local structures that could be damaged if the expandable structure 128 were expanded in an improper fashion. The clinician is also able to identify the expanded shape of the expandable structure 128 inside tissue based upon prior analysis of the morphology of the target site using, for example, plain film x-ray, fluoroscopic x-ray, or MRI or CT scanning. When the expandable structure 128 is used in bone in combination with a hardenable material, the expanded shape inside is selected to optimize the formation of a cavity that, e.g., when filled with the hardenable material, provides support across the region of the bone being treated. The expandable structure 128 is typically sized such that at least 25, 50, 75, or 90, % of cancellous bone 16 should be compressed.

The step of expanding the expandable member 126 may result in contacting tissue with the expandable structure 128, such as cancellous bone 16. In some configurations, the step of expanding the expandable structure 128 to form a cavity is further defined as expanding the expandable structure 128 in a position radially offset from the longitudinal axis A of the access cannula 18.

The method further comprises locking the expandable member 126 in place such that the expandable member 126 is restricted from moving in a longitudinal direction with respect to the access cannula 18. The expandable member 126 may be locked in position relative to the hub 28 of the deformable conduit assembly 26, thus statically defining the position of the expandable structure 128 with respect to the access cannula 18. This locking may allow independent motion of the deformable conduit 24 relative to the expandable structure 128.

Referring to FIG. 27, the method may further comprise retracting the deformable conduit 24 in a longitudinal direction relative to the access cannula 18 while the expandable member 126 remains in a substantially constant position with respect to the access cannula 18 such that at least a portion of the expandable structure 128 becomes at least partially uncovered by the deformable conduit 24. The expandable structure 128 may be fully uncovered, or may be uncovered by only 25, 35, 45, 55, 65, 75, or 85 or more, %, based on the longitudinal dimension of the expandable structure 128. In embodiments where the expandable structure 128 is not fully uncovered, the method may comprise expanding the expandable structure 128 while the expandable structure 128 remains at least partially disposed and constrained within the deformable conduit 24. This may allow the clinician to more directly control the shape of the cavity created by the expandable structure. The clinician may use indicia (visible, tactile, or audible) provided with the deformable conduit 24 or expandable structure 128 to set the amount of desired exposure of the expandable member 126.

Referring again to FIG. 24, the method includes placing an implant 140 into the tissue through the access cannula 18 or the deformable conduit 24. The step of placing the implant 140 may further comprise injecting the hardenable material into the channel formed by the steerable assembly 20. Alternatively, the step of placing the implant 140 may further comprise placing the hardenable material through the deformable conduit 24. In certain embodiments, the method comprises locking the implant delivery system 142 in place with respect to the access cannula 18 and the hub 28 of the deformable conduit 24, which allows the deformable conduit 24 to move axially with respect to the implant delivery system 142, without substantially moving the implant delivery system 142 or the access cannula 18. Along these lines, the method may comprise retracting the deformable conduit 24 in a longitudinal direction relative to the access cannula 18 while simultaneously urging hardenable material through the deformable conduit 24. This allows the hardenable material to occupy the entire channel once occupied by the deformable conduit 24 in the tissue to be displaced. The retraction may be performed gradually at a variety of speeds.

It is to be understood that the appended claims are not limited to express and particular systems or methods described in the detailed description, which may vary between particular embodiments that fall within the scope of the appended claims.

It is also to be understood that any ranges and subranges relied upon in describing various embodiments of the present invention independently and collectively fall within the scope of the appended claims and are understood to describe and contemplate all ranges, including whole and/or fractional values therein, even if such values are not expressly written herein. One of skill in the art readily recognizes that the enumerated ranges and subranges sufficiently describe and enable various embodiments of the present invention and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims and may be relied upon individually and/or collectively and provide adequate support for specific embodiments within the scope of the appended claims.

In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention has been described in an illustrative manner and it is to be understood that the terminology which has been used is intended to be in the nature of words of description rather than of limitation. Many modifications and variations of the present invention are possible in light of the above teachings and the invention may be practiced otherwise than as specifically described.

What is claimed is:

1. A system for manipulating tissue, the system comprising:
    an access cannula for insertion in the tissue;
    a steerable assembly comprising a steering instrument and a conformable nozzle, the steering instrument capable of assuming a first configuration substantially coaxial with the longitudinal axis of the access cannula and a second configuration that is not substantially coaxial with the longitudinal axis of the access cannula,
    wherein the steering instrument comprises a deflection mechanism operably attached to distal portion of the steering instrument such that when the deflection mechanism of the steering instrument is activated, the degree of curvature of the distal end of the steering instrument is changed relative to the longitudinal axis of the access cannula with the conformable nozzle tracking the orientation of the steering instrument and defining a curved configuration, and
    wherein the distal end of steering instrument is adapted to relax and flex freely in an unrestrained mode to permit retracting the distal end of the steering instrument from the conformable nozzle in the curved configuration with the conformable nozzle capable of retaining the curved configuration after retraction of the steering instrument.

2. The system of claim 1, wherein the deflection mechanism comprises a wire.

3. The system of claim 1, wherein the actuator comprises a trigger.

4. The system of claim 1, wherein the steering instrument comprises a plurality of hinge joints and a spine.

5. The system of claim 1, further comprises a stylet.

6. The system of claim 1, further comprising a curette comprising shape memory material.

7. The system of claim 1, wherein the actuator is configured for stepwise adjustment.

8. The system of claim 1, wherein the steering instrument comprises a sharp tip.

9. The system of claim 1, further comprising a balloon assembly.

10. A surgical method for manipulating tissue, which utilizes an access cannula and a steerable assembly, wherein the steerable assembly comprises a steering instrument and a conformable nozzle, with the steering instrument removably disposed within the conformable nozzle, wherein the steering instrument comprises a deflection mechanism operably attached to distal portion of the steering instrument such that when the steering instrument activated, the degree of curvature of the distal end of the steering instrument is changed relative to the longitudinal axis of the access cannula, the method comprising:

positioning the access cannula in the tissue to be manipulated;

inserting the steerable assembly through the access cannula such that the steerable assembly protrudes from the distal end of the access cannula;

activating the steering instrument such that the steering instrument assumes a configuration that is not substantially coaxial with the longitudinal axis of the access cannula; and retracting the steering instrument from the conformable nozzle with the conformable nozzle retaining the configuration that is not substantially coaxial with the longitudinal axis of the access cannula.

11. The method of claim 10, further comprising inserting a balloon through the conformable nozzle.

12. The method of claim 10, further comprising injecting cement through the conformable nozzle.

* * * * *

UNITED STATES PATENT AND TRADEMARK OFFICE
CERTIFICATE OF CORRECTION

| | | |
|---|---|---|
| PATENT NO. | : 9,839,443 B2 | Page 1 of 1 |
| APPLICATION NO. | : 13/923104 | |
| DATED | : December 12, 2017 | |
| INVENTOR(S) | : Christopher Scott Brockman et al. | |

It is certified that error appears in the above-identified patent and that said Letters Patent is hereby corrected as shown below:

In the Claims

In Column 26, Line 44, Claim 1:
Please change "a deflection mechanism operably attached to distal portion" to "a deflection mechanism operably attached to a distal portion".

In Column 26, Line 52, Claim 1:
Please change "wherein the distal end of steering instrument is adapted" to "wherein the distal end of the steering instrument is adapted".

In Column 26, Line 61, Claim 3:
Please change "wherein the actuator comprises a trigger." to "wherein an actuator comprises a trigger.".

In Column 26, Line 65, Claim 5:
Please change "further comprises a stylet." to "further comprising a stylet.".

In Column 27, Line 1, Claim 7:
Please change "wherein the actuator is configured for stepwise adjustment." to "wherein an actuator is configured for stepwise adjustment.".

In Column 27, Line 14, Claim 10:
Please change "a deflection mechanism operably attached to distal portion" to "a deflection mechanism operably attached to a distal portion".

In Column 27, Line 15, Claim 10:
Please change "when the steering instrument activated" to "when the steering instrument is activated".

Signed and Sealed this
Fourteenth Day of August, 2018

Andrei Iancu
*Director of the United States Patent and Trademark Office*